(12) United States Patent
Chow et al.

(10) Patent No.: US 9,034,439 B2
(45) Date of Patent: May 19, 2015

(54) SYNTHESIS AND APPLICATIONS OF SOLUBLE PENTACENE PRECURSORS AND RELATED COMPOUNDS

(75) Inventors: Tahsin J. Chow, Taipei (TW);
Chung-Chih Wu, Taipei (TW);
Ta-Hsien Chuang, Kaohsiung (TW);
Hsing-Hung Hsieh, Changhua (TW);
Hsin-Hui Huang, Taipei (TW)

(73) Assignee: Academia Sinica, Taipei (TW)

( * ) Notice: Subject to any disclaimer, the term of this patent is extended or adjusted under 35 U.S.C. 154(b) by 92 days.

(21) Appl. No.: 13/539,520

(22) Filed: Jul. 2, 2012

(65) Prior Publication Data
US 2013/0017497 A1 Jan. 17, 2013

Related U.S. Application Data

(63) Continuation of application No. 12/395,920, filed on Mar. 2, 2009, now Pat. No. 8,277,903.

(60) Provisional application No. 61/033,466, filed on Mar. 4, 2008.

(51) Int. Cl.
| | |
|---|---|
| *C07C 25/22* | (2006.01) |
| *C07C 49/665* | (2006.01) |
| *C07C 49/683* | (2006.01) |
| *C07C 49/753* | (2006.01) |
| *C07D 333/08* | (2006.01) |
| *C07C 205/45* | (2006.01) |
| *C07C 255/56* | (2006.01) |
| *B05D 1/32* | (2006.01) |
| *B05D 3/02* | (2006.01) |
| *B05D 3/06* | (2006.01) |
| *H01L 51/00* | (2006.01) |

(52) U.S. Cl.
CPC ............... *C07C 25/22* (2013.01); *B05D 1/327* (2013.01); *B05D 3/0254* (2013.01); *B05D 3/06* (2013.01); *C07C 49/665* (2013.01); *C07C 49/683* (2013.01); *C07C 49/753* (2013.01); *C07C 205/45* (2013.01); *C07C 255/56* (2013.01); *C07C 2103/86* (2013.01); *C07C 2103/90* (2013.01); *C07D 333/08* (2013.01); *H01L 51/0003* (2013.01); *H01L 51/0055* (2013.01); *H01L 51/0068* (2013.01); *Y02E 10/549* (2013.01)

(58) Field of Classification Search
CPC .. C07C 205/45; C07C 255/56; C07C 49/683; C07C 49/753; C07C 2103/90; C07C 2103/86; C07C 49/665; C07D 333/08; H01L 51/0003; H01L 51/0068; H01L 51/0055; Y02E 10/549
USPC .......... 568/300, 303, 308, 325, 326, 327, 329, 568/959, 367; 427/555, 515
See application file for complete search history.

(56) References Cited

U.S. PATENT DOCUMENTS

| | | |
|---|---|---|
| 6,963,080 B2 | 11/2005 | Afzali-Ardakani |
| 2003/0136964 A1 | 7/2003 | Afzali-Ardakani et al. |
| 2003/0144562 A1 | 7/2003 | Afzali-Ardakani et al. |
| 2004/0119073 A1 | 6/2004 | Ardakami et al. |

FOREIGN PATENT DOCUMENTS

| | | | |
|---|---|---|---|
| CN | 1585151 A | 2/2005 | |
| WO | 2004/083160 A1 | 9/2004 | |
| WO | 2006125504 A1 | 11/2006 | |
| WO | WO 2006/125504 | * 11/2006 | .............. H01L 51/05 |

OTHER PUBLICATIONS

Lai et al. (Journal of Chemical Theory and Computation 2006 vol. 2 pp. 1078-1084).*
Tanida et al. (Tetrahedron Letters No. 49 pp. 4331-4334 1970).*
Chen et al. (Chemical Communications 2007 pp. 1065-1067).*

* cited by examiner

*Primary Examiner* — Patrick Ryan
*Assistant Examiner* — Aaron Greso
(74) *Attorney, Agent, or Firm* — Harness, Dickey & Pierce, PLC

(57) ABSTRACT

The present disclosure relates to methods and systems for synthesis of bridged-hydropentacene, hydroanthracene and hydrotetracene from the precursor compounds pentacene derivatives, tetracene derivatives, and anthracene derivatives. The invention further relates to methods and systems for forming thin films for use in electrically conductive assemblies, such as semiconductors or photovoltaic devices.

Figure 1:
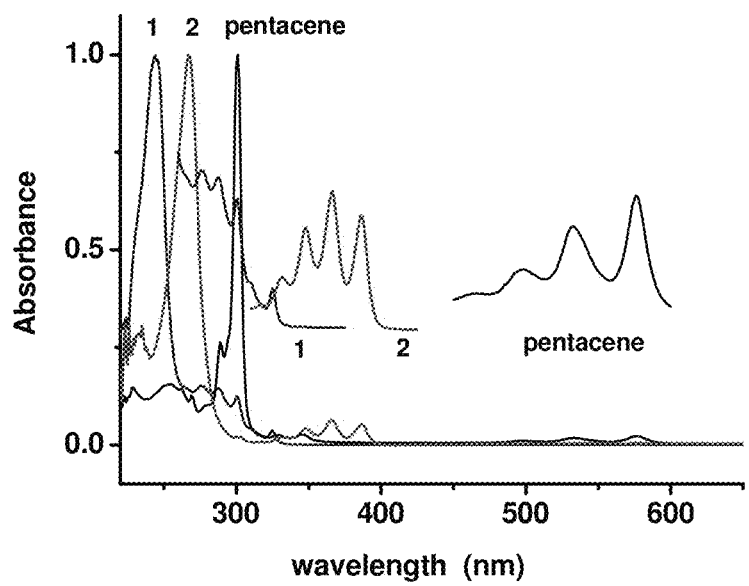

7 Claims, 8 Drawing Sheets
(7 of 8 Drawing Sheet(s) Filed in Color)

SYNTHESIS AND APPLICATIONS OF SOLUBLE PENTACENE PRECURSORS AND RELATED COMPOUNDS

CROSS-REFERENCE TO RELATED APPLICATIONS

This application is a continuation of U.S. patent application Ser. No. 12/395,920 filed on Mar. 2, 2009 which claims the benefit of U.S. Provisional Application No. 61/033,466, filed on Mar. 4, 2008. The entire disclosures of the above applications are incorporated herein by reference.

FIELD

The present disclosure relates to methods and systems for synthesis of pentacene precursors and other oligoacene precursors, such as ketone-bridged hydropentacenes having at least one of a 1,4-, 5,14-, or 6,13-bridge and their corresponding ketals, which can be used in solution processes to efficiently form thin films containing pentacene or other oligoacene(s). Also disclosed are methods and systems for forming such thin films for use in electrically conductive assemblies, such as semiconductors or photovoltaic devices.

BACKGROUND

The statements in this section merely provide background information related to the present disclosure and may not constitute prior art.

Pentacene is recognized as a good organic semi-conducting material for use in p-type organic thin film transistors (OTFT), due to its high charge mobility. It is currently known that pentacene can be prepared by volatile decarbonylation of a 6,13-bridged-6,13-dihydropentacene precursor, e.g., by heating to 150° C. to liberate carbon monoxide. This precursor is reported to have some degree of solubility in a limited number of organic solvents such as chloroform and might therefore be amenable to spin coating using multiple castings, e.g., coats.

The characteristics of pentacene can be attributed to its high degree of crystallinity in the solid state. However, the high tendency of crystallization also renders its low degree of solubility in organic solvents. Therefore it becomes difficult to prepare thin films through solution processes. In an effort to address this shortcoming, scientists at Philips and IBM have developed a strategy of preparing precursors of pentacene that are soluble in organic solvents, and are able to produce pentacene after the films are prepared. The structures of pentacene precursor are usually cyclo-adducts of pentacene itself (acting as a diene) with another small volatile fragment (acting as a dienophile). After a film is produced by spin coating processes, relatively pure pentacene can be regenerated upon heating through a retro-cyclization process.

Since the purity of pentacene is crucial to the conductivity of films, the volatile fragment(s), which is released during the thermal process, should be expelled out of the crystal lattice as much as possible. The yield of retro-cyclization must be high, and the smaller the leaving fragment the better. Heavy elements such as sulfur and chlorine, which have been present in many leaving groups of previous examples, are known to readily contaminate the resultant films. The preparation of a pentacene precursor, i.e. compound 1, which extrudes a unit of carbon monoxide at 150° C., has been described by Chen et al. The small size and inert nature of carbon monoxide render it the best candidate for serving as a leaving fragment. The pentacene film thus produced exhibited typical OTFT characteristics, i.e. an on/off current ratio about $1.2 \times 10^5$ and field-effect mobility μ close to 0.01 $cm^2V^{-1}s^{-1}$.

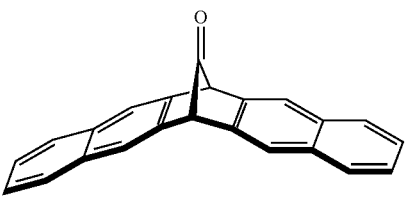

1

The solubility of compound 1 is a relatively low ~0.7 mg/mL in some common organic solvents, e.g. methylene chloride and THF. However, in order to prepare a film with required thickness therefrom, repeated casting processes are necessary.

However, it would be advantageous to provide a pentacene precursor having improved solubility in various organic solvents, as well as being capable of conversion to pentacene below 360° C. in a step that leaves little, it any, non-pentacene residue in the product. This would permit pentacene to be used in a larger range of commercial applications. Ideally, pentacene processes should be highly soluble in organic solvents such that a limited number of castings are required to obtain useful end-product. In addition to improved pentacene processes, anthracene and tetracene type-oligoacenes useful in organic semiconductor and/or photovoltaic applications are also disclosed and shall be readily processable in accordance with the teachings of the present invention.

SUMMARY

Various embodiments hereof provide general methods for the synthesis of bridged-hydropentacene, hydroanthracene and hydrotetracene. The precursor compounds disclosed herein can be referred to as: (1) pentacene derivatives, (2) tetracene derivatives, and (3) anthracene derivatives. Various embodiments hereof also include methods for carbon monoxide expulsion from aromatic hydrocarbon derivatives by both thermal and photochemical routes; methods for device fabrication therefrom; and devices prepared thereby, including semiconductor and photovoltaic devices; and methods of preparing, from the precursors, oligoacenes for use in conductive compositions, dye compositions, and others.

In some embodiments, the present description provides a general method for the synthesis of 1,4- and/or 5,14- and/or 6,13-bridged hydropentacenes useful as soluble precursors for formation of pentacene or substituted pentacenes, e.g., halopentacenes. In exemplary embodiments, the present subject matter provides improved synthetic methods for preparing bridged pentacene precursor compounds that contain at least one: 1,4-dihydro-1,4-(ketone or ketal) bridge; 5,14-dihydro-5,14-(ketone or ketal) bridge; 6,13-dihydro-6,13-(ketone or ketal) bridge; but not limited to one bridge; as well as novel compounds synthesized thereby. In various embodiments, the bridges can be ketone or ketal groups having from one to four carbon atoms (i.e., C1-C4). For ketone-bridges, a C1 ketone (i.e. oxomethylene) group is considered particularly useful. The oxomethylene group of a bridge hereof can also be referred to as a carbonyl group.

Thus, in various embodiments, synthetic methods hereof can be employed to produce pentacene precursor compounds, such as: 1,4-dihydro-1,4-oxomethylene-bridged pentacene; 5,14-dihydro-5,14-oxomethylene-bridged pentacene; 5,7,12, 14-tetrahydro-5,14:7,12-di(oxomethylene-bridged)pentacene; 1,4,8,11-tetrahydro-1,4:8,11-di(oxomethylene-bridged)pentacene; 1,4,6,8,11,13-hexahydro-1,4:6,13:8,11-tri(oxomethylene-bridged)pentacene; ketal-bridged compounds corresponding to any of these oxomethylene-bridged compounds; and halogenated versions of any of the foregoing, useful as halopentacene precursor compounds. Pentacene precursor compounds further include those illustrated in the various schemes shown below as well as halogenated versions thereof.

Reference herein to ketal-bridged compounds corresponding to such ketone (e.g., oxomethylene)-bridged pentacene precursor compounds indicates those compounds in which an oxygen atom and a carbon atom corresponding to those of an oxomethylene oxo group of the latter compound participate in either ketal (i.e. bis C1-C4 alkyl ether) or C1-C4 spiroketal formation, whereby the ketal group forms the bridge that corresponds to the oxomethylene bridge. Representative examples of such ketal bridging groups include: dimethyl ketal; ethylene spiroketal, i.e. (1,2-ethanediyl)spiroketal; and butylene spiroketal, i.e. (2,3-butanediyl)spiroketal groups. The spiroketals can be formed from C1-C4 diols, such as ethylene glycol or 2,3-butanediol. As used herein, "C1-C4 ketal group" refers to bis(C1-C4 alkyl) ketal groups and to C1-C4 spiroketal groups. Ketals include acetals derived from ketones by replacement of the oxo group by two hydrocarbyloxy groups $R_2C(OR)_2$, where $R \neq H$. Spiroketals include one carbon atom as the only common member of two rings.

In some embodiments hereof, halopentacene precursor compounds can be provided that have the structure of any of the above oxomethylene-bridged or ketal-bridged compounds and are further halogenated, e.g., chlorinated. Symmetrically halogenated halopentacene precursors are particularly useful in some embodiments. For example, 2,3,9,10-tetrahalo and 1,2,3,4,8,9,10,11-octahalo forms can be used, such as 2,3,9,10-tetrachloro or 1,2,3,4,8,9,10,11-octachloro precursor compounds. In some embodiments, halopentacene precursors can be dehalogenated to form pentacene precursors, or can be used to form halopentacenes that can in turn be dehalogenated to form pentacenes. Any dehalogenation treatments known as useful therefor in the art can be employed for this, e.g., treatment with sodium in tert-butanol and aromatization by dichloro dicyano quinone (DDQ) treatment.

Further areas of applicability will become apparent from the description provided herein. It should be understood that the description and specific examples are intended for purposes of illustration only and are not intended to limit the scope of the present disclosure.

DRAWINGS

The patent or application file contains at least one drawing executed in color. Copies of this patent with color drawings will be provided by the Patent and Trademark Office upon request and payment of necessary fee.

The drawings described herein are for illustration purposes only and are not intended to limit the scope of the present disclosure in any way.

FIG. 1 presents UV absorptions of compounds 1 (blue), 2 (red), and a thermally generated pentacene (black). The long wavelength bands are magnified to the center of graph.

Figure 2:
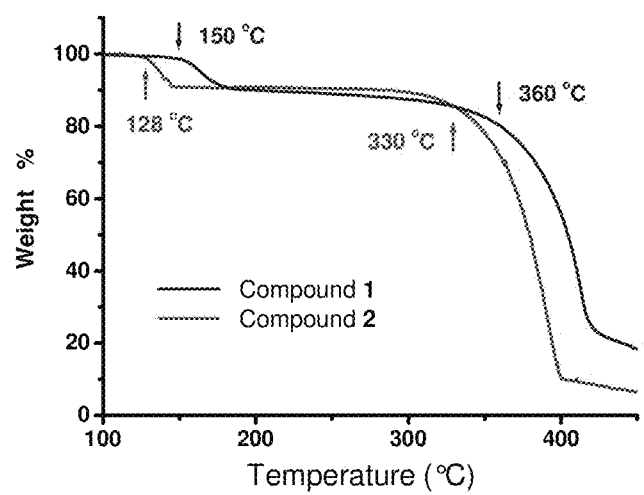

FIG. 2 presents thermogravimetric analysis curves for compounds 1 (blue) and 2 (red) at 10° C./min heating rate, assessing the carbon monoxide (CO) expulsion reaction, in which the carbonyl bridge is released from the precursor for conversion to pentacene. The CO expulsion reaction of 2 started at 128° C., better than the 150° C. for the start of reaction for 1, and the resulting pentacene was stable till 300° C.

Figure 3A:
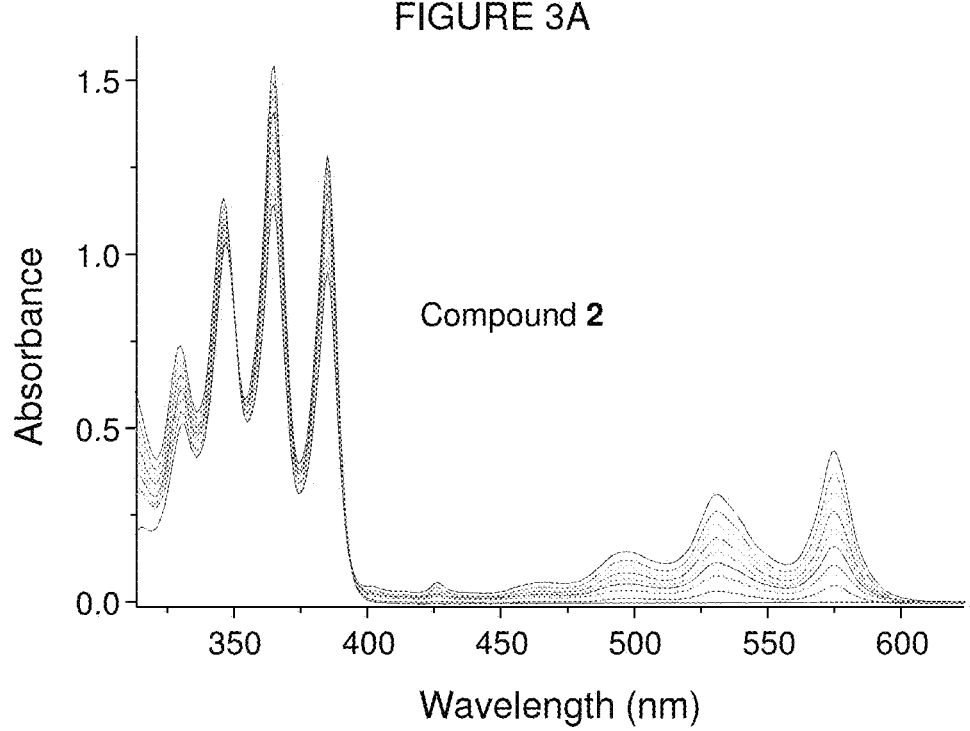
Figure 3B:
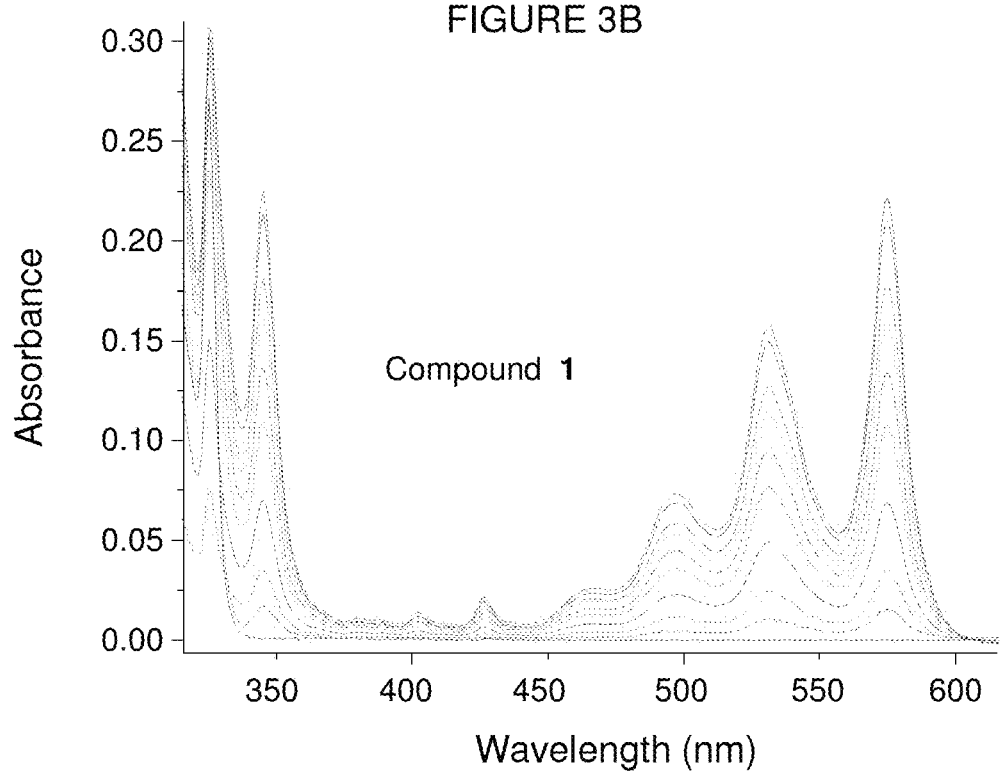

FIG. 3A presents absorption spectra of 2, in degassed tetrahydrofuran (THF), obtained upon irradiation with 366 nm UV light with different exposure times, 0 to 40 sec, with increments of 5 sec. FIG. 3B presents comparable absorption spectra of 1, in degassed THF, irradiated at 310 nm as a function of exposure times of 0 to 40 sec, with increments of 5 sec.

Figure 4:
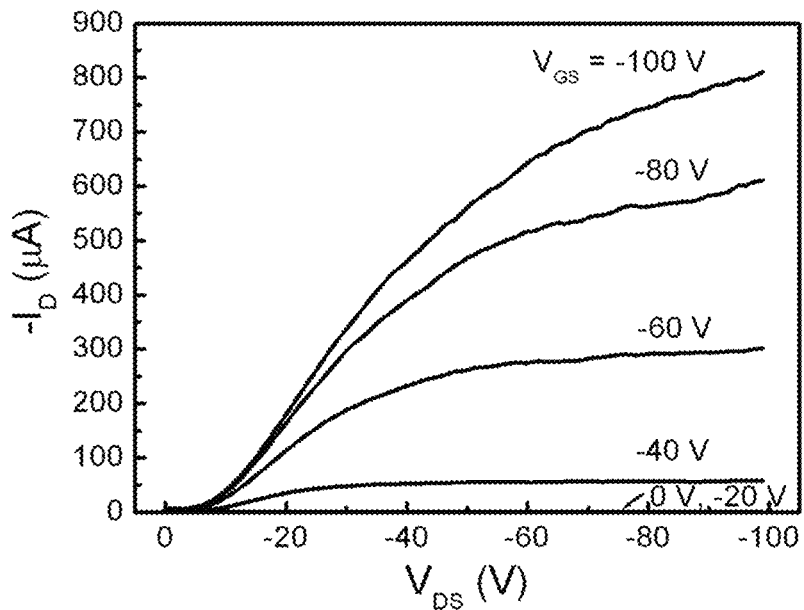

FIG. 4 presents plots of drain current $I_D$ versus drain-source voltage ($V_{DS}$) at various gate voltages ($V_{GS}$) obtained from an OTFT with a channel width of 20 cm and a channel length of 10 μm.

Figure 5:
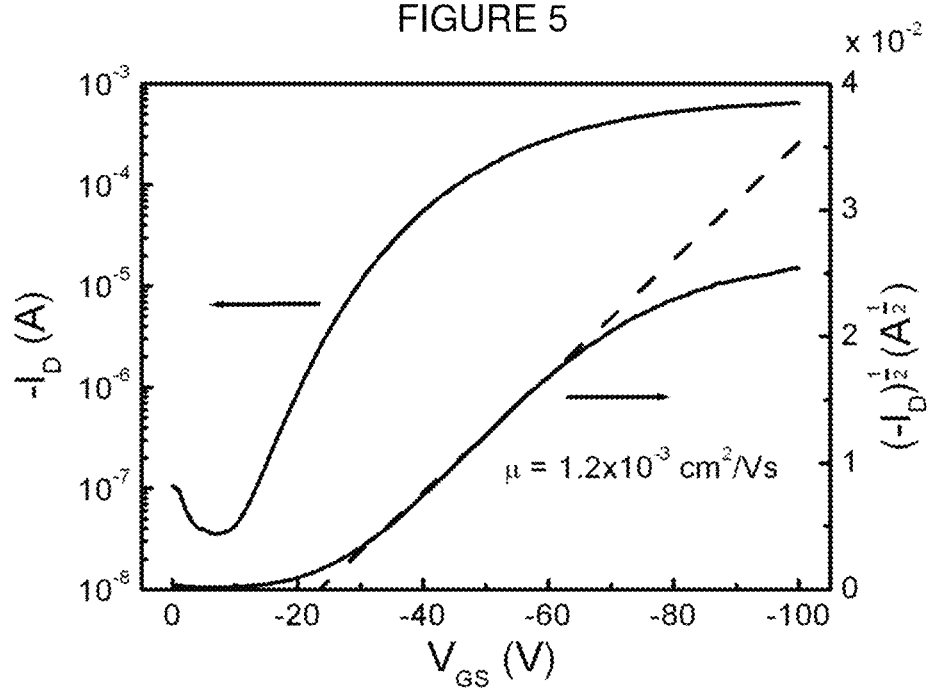

FIG. 5 presents plots of $\log(I_D)$ vs. $V_{GS}$ for $V_{Ds}=-80V$, and $\sqrt{I_D}$ vs. $V_{GS}$ in the saturation.

Figure 6:
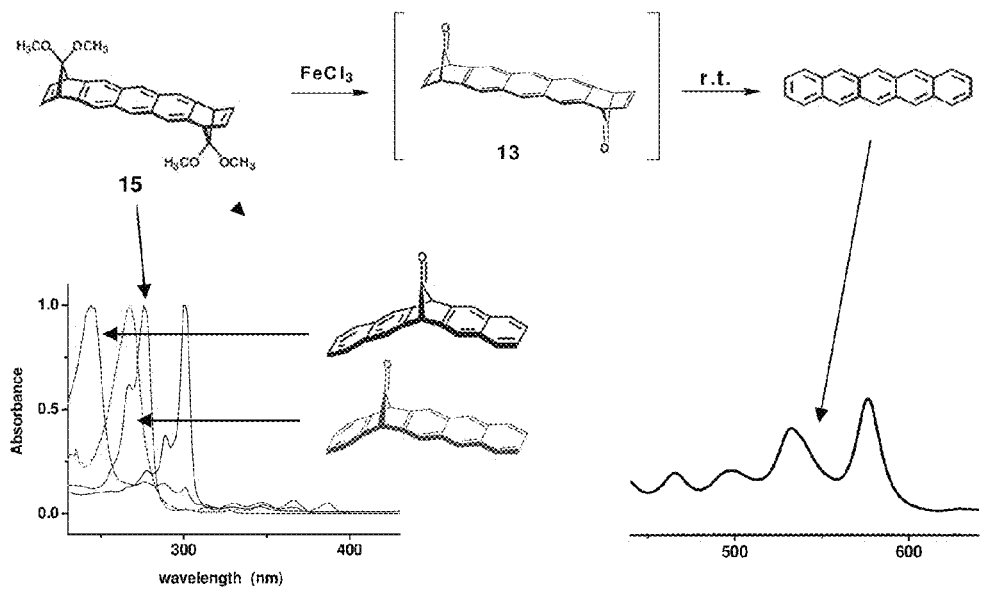

FIG. 6 presents results for a dimethyl ketal-bridged pentacene precursor.

Figure 7:
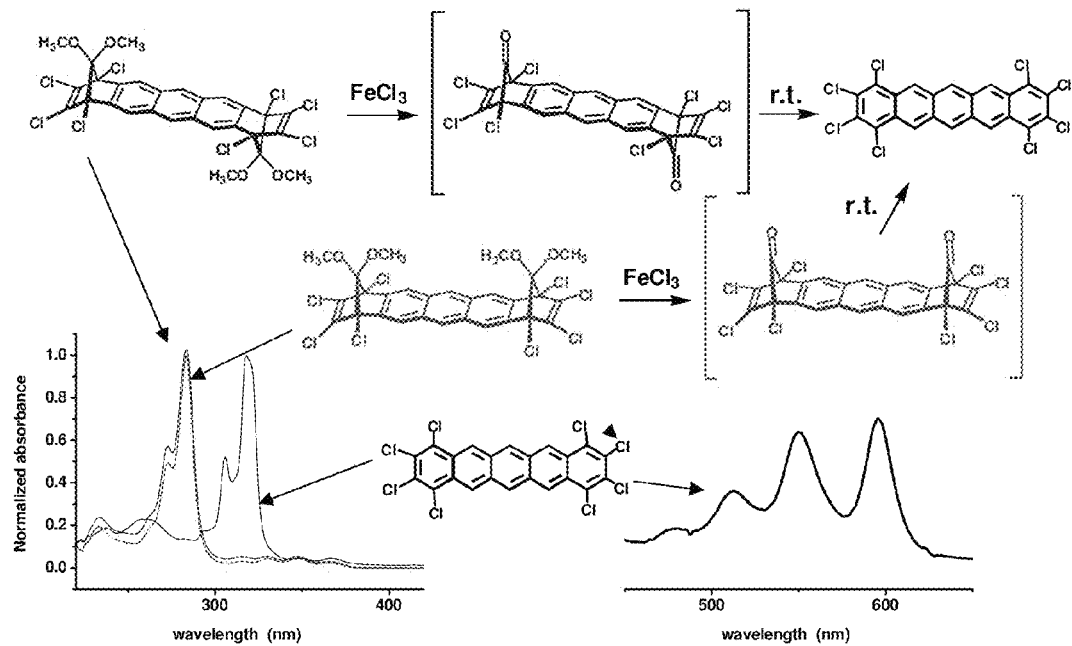

FIG. 7 presents results for a dimethyl ketal-bridged halopentacene precursor.

Figure 8:
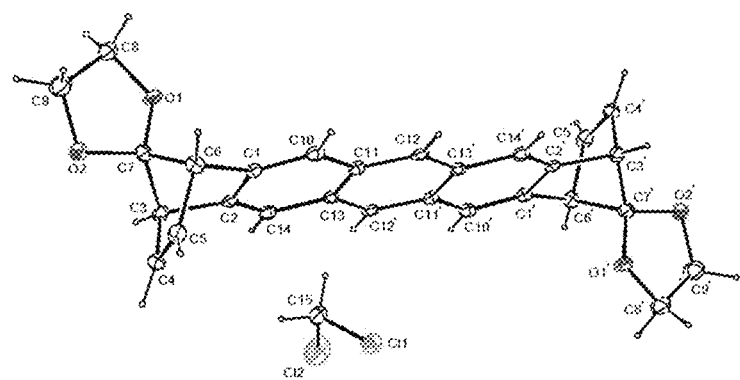

FIG. 8 presents an X-ray diffraction structure for compound 16.

Figure 9:
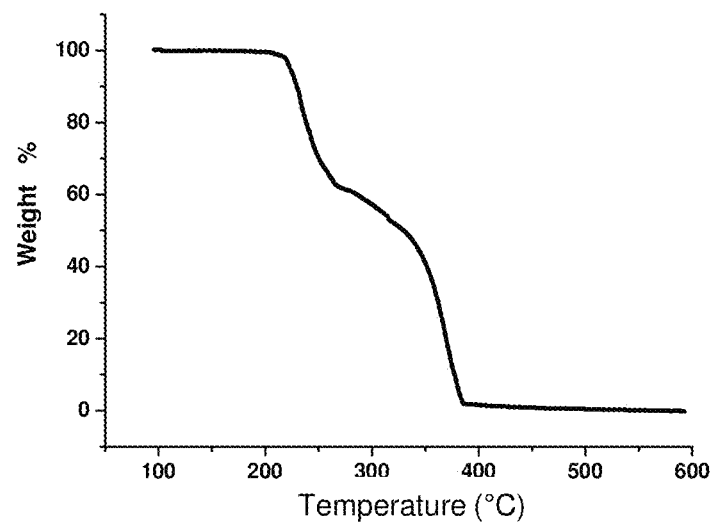

FIG. 9 presents a thermogravimetric analysis (TGA) plot for compound 16.

Figure 10:
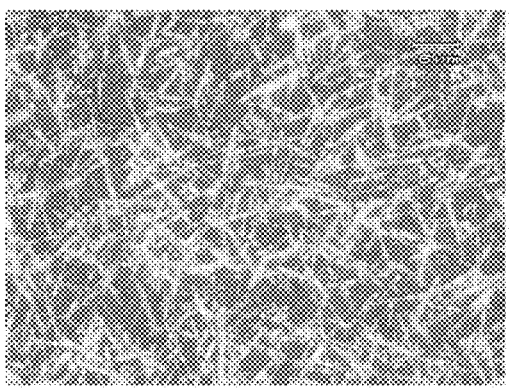

FIG. 10 presents an image of a film made of compound 1.

Figure 11:
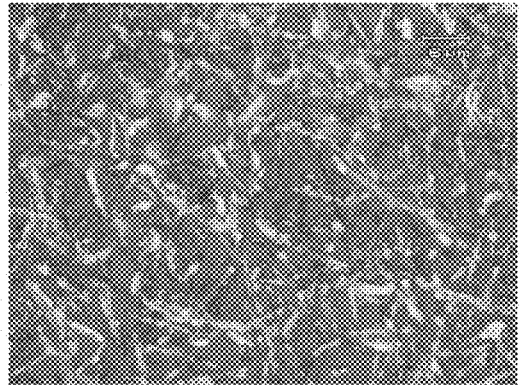

FIG. 11 presents an image of a web-like pentacene film, formed from compound 1, after it has been heated to its conversion temperature.

Figure 12A:
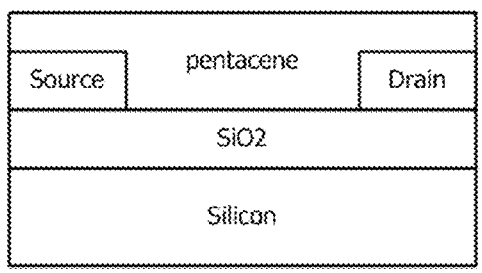
Figure 12B:
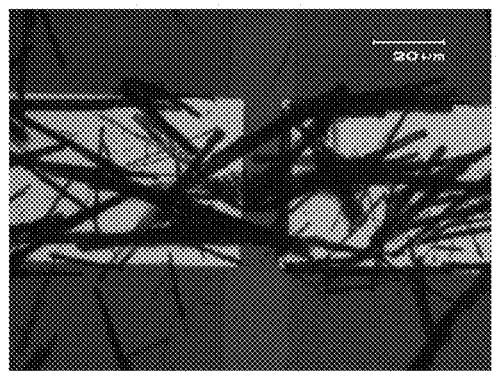

FIGS. 12A and 12B present, respectively, a schematic of the structure and a photographic image of the material of OTFT devices made from compounds 1 and 2.

Figure 13A:
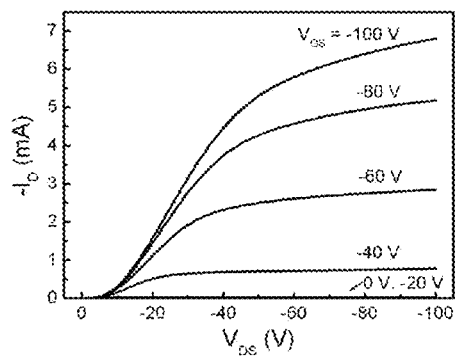
Figure 13B:
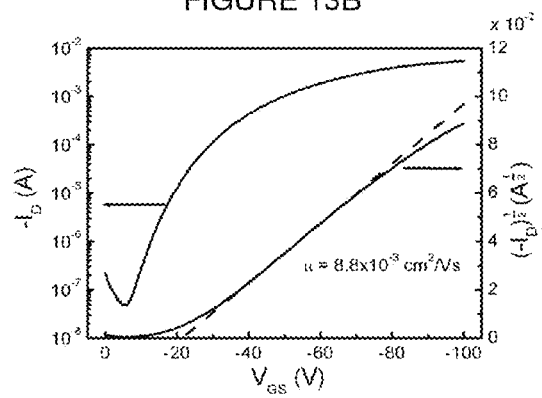

FIGS. 13A and 13B present graphs of test results showing typical field-effect transistor (FET) characteristics of a device made from compound 1, which are: $\mu=8.8\times10^{-3}$ cm$^2$ V$^{-1}$ s$^{-1}$ and on/off current ratio $\sim 1.2\times10^5$.

Figure 14A:
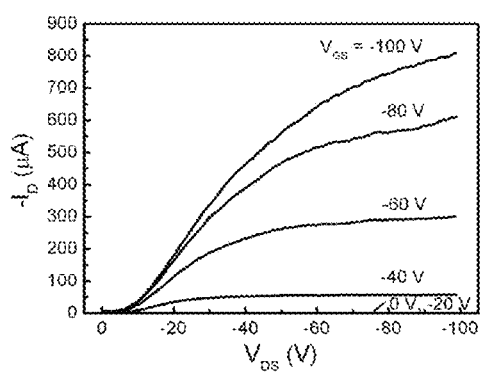
Figure 14B:
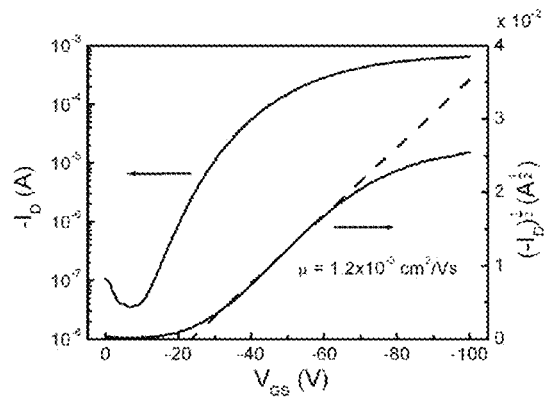

FIGS. 14A and 14B present graphs of test results showing typical FET characteristics of a device made from compound 2, which are: $\mu=1.2\times10^{-3}$ cm$^2$ V$^{-1}$ s$^{-1}$ with on/off current ratio $\sim 1.82\times10^4$.

Figure 15A:
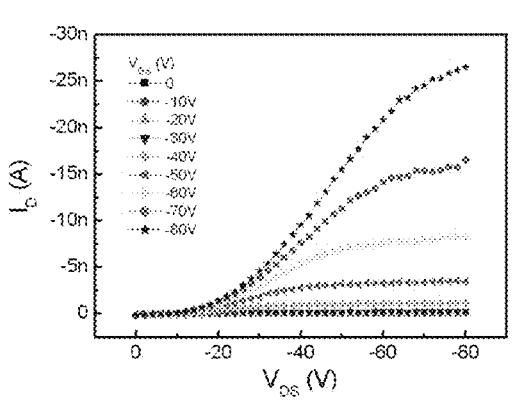
Figure 15B:
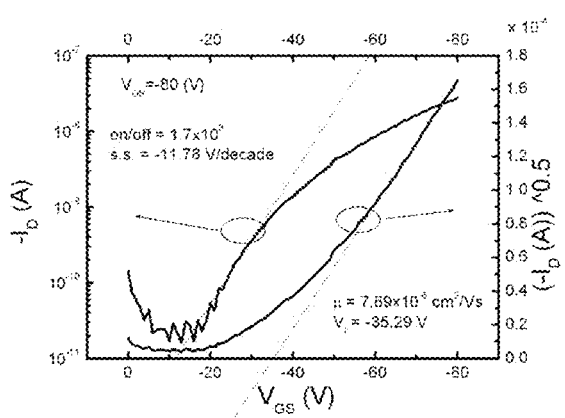

FIGS. 15A and 15B present graphs of test results showing typical FET characteristics of a device made from compound 16. Parameters obtained from a device of channel width of 1 mm and channel length of 5 μm are: field-effect mobility $\mu=7.89\times10^{-6}$ cm$^2$/Vs, and estimated on/off current ratio=$1.7\times10^3$. FIG. 15A presents plots of drain current $I_D$ versus drain-source voltage $V_{DS}$ at various gate voltages $V_{GS}$ obtained from an OTFT with a channel width of 1 mm and a channel length of 5 μm. 15B presents plots of $\log(I_D)$ vs. $V_{GS}$ for $V_{DS}=-80$ V, and $\sqrt{I_D}$ vs. $V_{GS}$ in the saturation mode. The device made from 13 performed worse than those made from 1 and 2, because at a higher anneal temperature the substrates tend to evaporate from the surface of the film. Therefore it was difficult to maintain an ideal film thickness.

Figure 16:
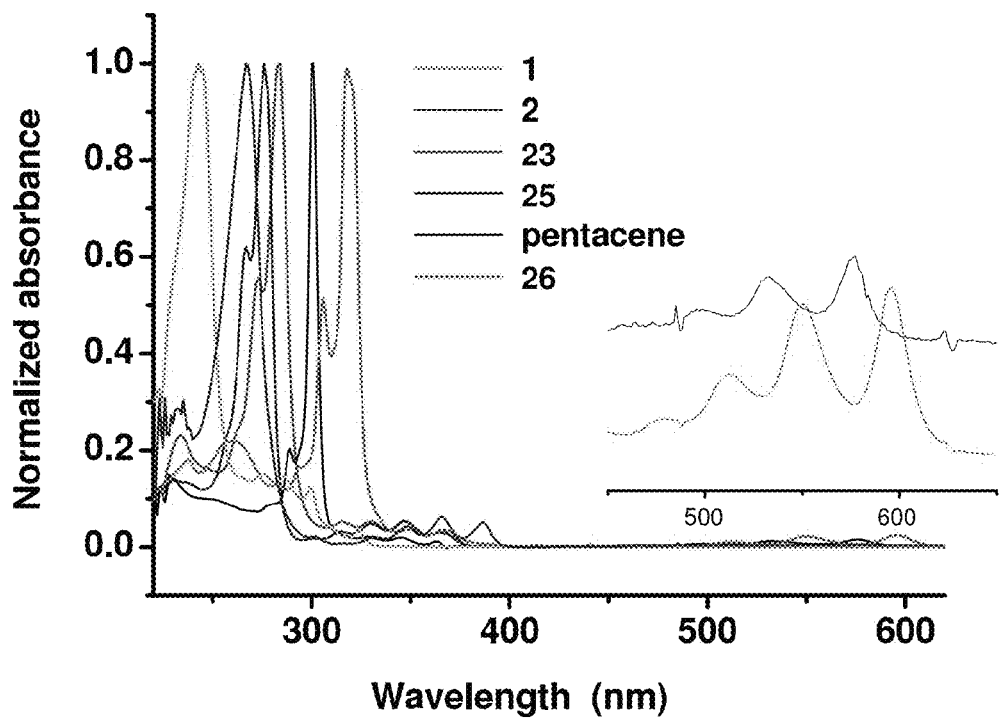

FIG. 16 presents normalized UV absorptions of compounds 1 (green), 2 (brown), 25 (blue), 23 (red), pentacene (black), and 26 (pink). The pentacene and compound 26 were produced by acidic hydrolysis of 25 and 23, respectively. The inset shows the characteristic long wavelength absorptions of pentacene (black) and 26 (pink).

Figure 17:
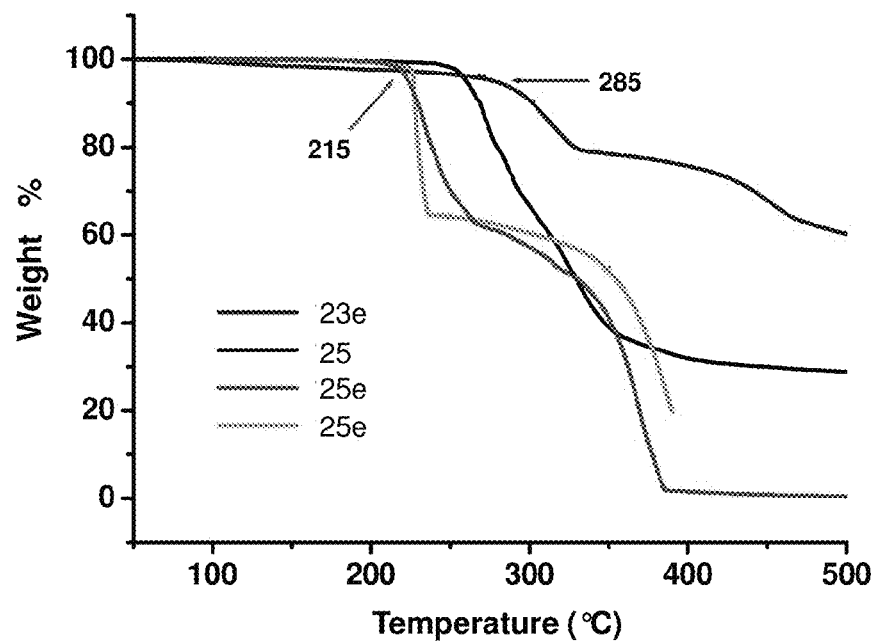

FIG. 17 presents thermogravimetric analyses (TGA) of compound 23e (blue), 25 (black), and 25e (red) at 10° C./min heating rate. The weight losses of 23e and 25e correspond correctly to the production of pentacene upon expulsion of $CO_2$ and ethylene units. A better fragmentation can be obtained by slowing down the heating rate to 0.13° C./min between 230-240° C. (green), so that the evaporation of pentacene can also be slowed down.

DETAILED DESCRIPTION

The following description is merely exemplary in nature and is not intended to limit the present disclosure, application, or uses. Among oligoacene precursors provided herein are precursors for anthracene (A), tetracene (B), and pentacene (C), whose respective structures are shown below.

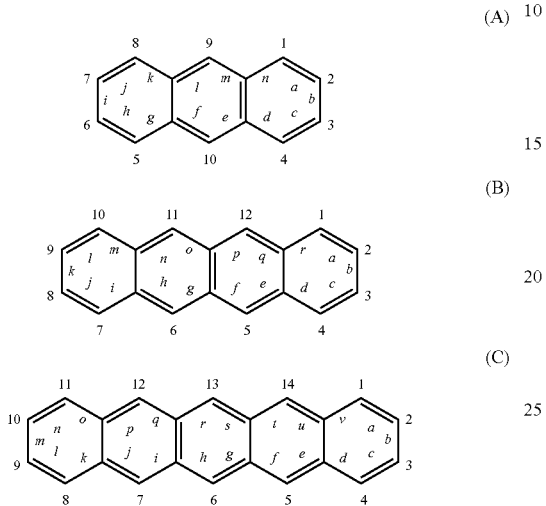

In various embodiments, the precursors possess higher solubility than previously known precursors for a given oligoacene. In some embodiments, the precursors hereof possess different bridging group chemistries and/or bridging architectures than those of such previously known oligoacene precursors. Precursors for pentacenes are described below, followed by descriptions of tetracene and anthracene precursors hereof.

In various embodiments hereof, relatively higher solubility of pentacene and other oligoacene precursors available through the synthetic methods described herein, allows for the preparation of large films by spin-coating processes. Substantially pure pentacene and other oligoacene film can thereby be generated either thermally or photochemically. OTFT devices made from these materials exhibit typical FET characteristics and are useful in any industry that uses organic thin film transistors (OTFT). Applications can be extended to organic integrated circuits, active-matrix flat-panel displays (AMLEDs such as OLEDs), radio frequency identification (RF-ID), photovoltaic cells, chemical sensors, and other flexible electronics, by way of non-limiting example.

Various embodiments of new compounds provided herein are soluble in organic solvents, so that they can be processed into large films by, e.g., a spin-coating technique. The pentacene precursors are capable of producing pentacene either thermally or photochemically by extruding, i.e. releasing, volatile units of CO or $CO_2$, as can other precursors hereof to their oligoacenes.

In thermal routes, the pentacene precursor fragmentation temperature (from ambient to 240° C.) is well below the thermal decomposition temperature of pentacene (360° C.), while in some cases the fragmentation can also be initiated by photo-irradiation. The production yield is nearly quantitative, thus generating pentacene in very high purity. The molecular fragments expelled from the precursor compounds during conversion to pentacene were small organic molecules that are chemically inert and highly volatile. The high purity of resulting pentacene films is evidenced in OTFT devices, which exhibit typical thin-film transistor (TFT) characteristics.

Representative Pentacene Carbonyl Adducts.

Designing electronic devices made of organic materials is of intensive current interest, and organic thin-film transistor (OTFT) is an essential part of it. The most well-known organic gate material for OTFT so far is pentacene, which is a p-type semiconductor with good charge mobility.

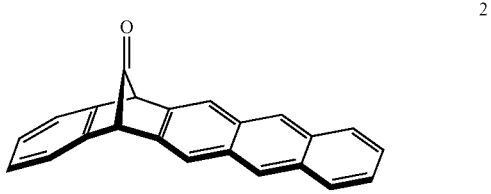

In order to obtain improved p-type semiconductors, it has been discovered that using pentacene precursors having off center bridging of ketone/carbonyl or ketal groups, such as that shown in compound 2, give rise to compositions having enhanced solubility over precursors formed from compound 1. It has been unexpectedly found that, even with only a slight increase of solubility, substantial improvement of the spin casting process can be obtained by compounds prepared according to the various embodiments hereof. Compound 2 can be synthesized as described below.

The synthetic pathway can be depicted in Scheme 1A, which starts from a [4+2] cycloaddition of a furan derivative 3 (dihydroisonaphthofuran) with a benzonorbornadiene derivative 4 (benzo-(7-isopropylidene)norbornadiene). The adduct 5 was obtained in 72% yield, and possesses the basic skeleton of pentacene with five fused rings. Its $C_{2v}$ symmetrical geometry was affirmed by the presence of 14 distinctive absorption signals in $^{13}C$ NMR spectrum. The two methylene hydrogens appear in $^1H$ NMR spectrum as two separate doublets at δ 3.27 and 3.57 with a large coupling constant (20 Hz). Aromatization of the forth ring of 5 was achieved by an oxidation with dicyanodichloroquinone (DDQ), while 6 was obtained in a quantitative yield. The three types of methinyl hydrogens exhibit three singlets at δ 1.99, 3.93, and 5.33 in $^1H$ NMR field. Further dehydration/aromatization under the catalysis of toluenesulfonic acid resulted to a complex mixture of compounds 7, 8 and 9 in a total yield of 75%. Their relative ratio depends on the concentration of acid as well as the time of reaction. The quaternary carbon of 7, which bears the hydroxyl group, shows a singlet signal at δ 71.5 in $^{13}C$ NMR spectrum. Compounds 8 and 9 are believed to be the secondary products deriving from 7. The optimal yield of 9, which was considered to be a suitable precursor of 2, was less than 10%. To improve the yield toward desired product, compound 6 was first treated with meta-chloro-perbenzoic acid (m-CPBA) to form an epoxide, followed by an acid catalyzed rearrangement. The diol 10 was obtained in 74% as the main product. The presence of a 1,2-diol was evidenced by a strong absorption band at 3450-3550 $cm^{-1}$ in IR spectrum, and the two quaternary carbon signals at δ 74.3 and 105.5 in $^{13}C$ NMR spectrum. Oxidation of 10 by iodobenzene diacetate $(PhI(OAc)_2)$ cleaved the C—C bond to give the desired ketone 2 in 76% yield. The carbonyl group shows a strong absorption at 1782 $cm^{-1}$ in IR, and a low field peak at δ 192.2 in $^{13}C$ NMR. The optimal overall yield from (3+4) to 2 was 40%.

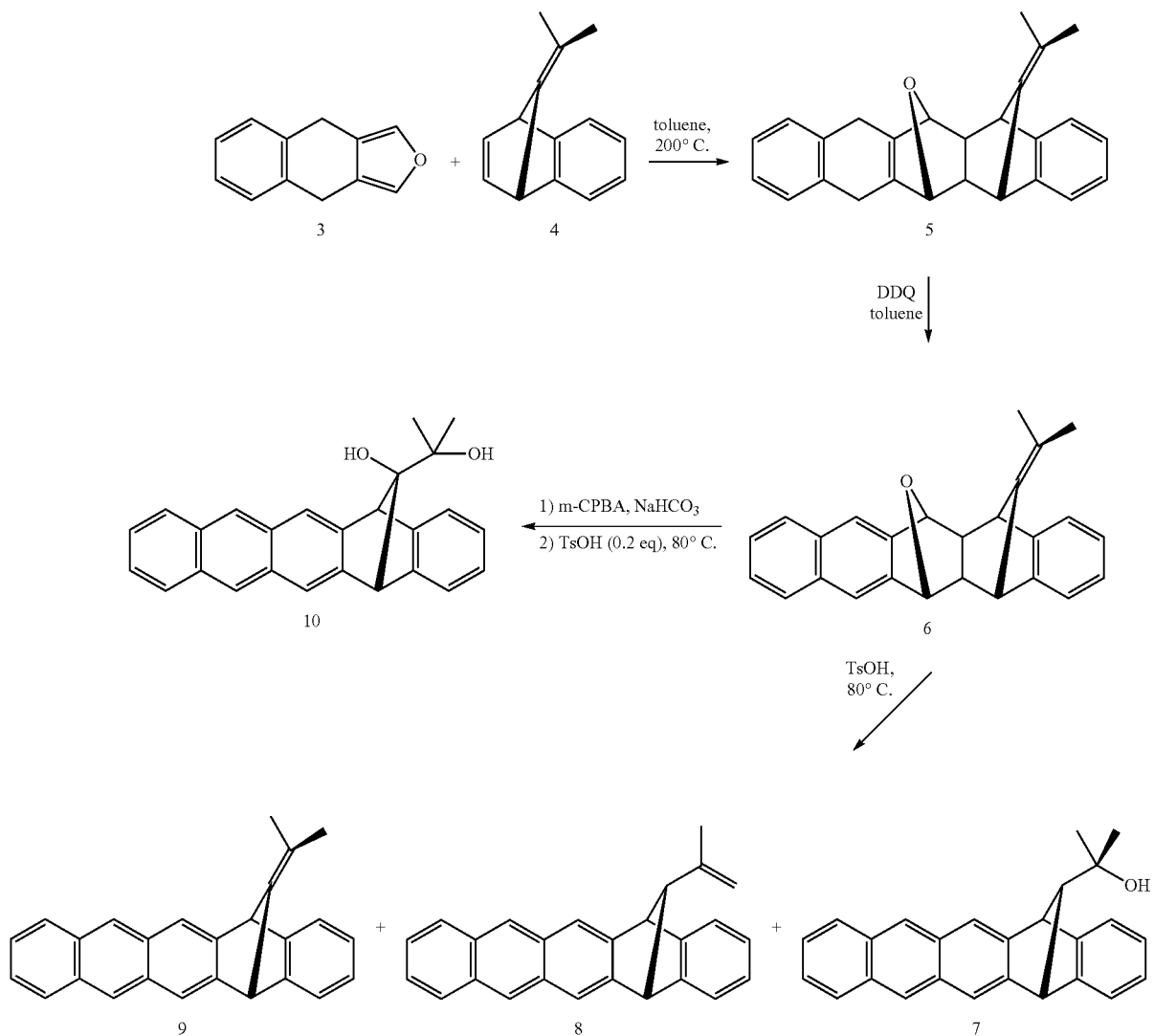

Scheme 1A

Ketone 2 can also be made from 9 through ozonolysis in a mixed solvent (CH$_2$Cl$_2$:MeOH=2:1) at −35° C., followed by a reduction of the ozonide intermediate with dimethylsulfide, however, this method is not preferred for the production of compound 2. The UV absorption spectrum of compound 2 is significantly different from that of compound 1 (FIG. 1). A strong π-π* transition ($^1$A→$^1$B) of compound 2 gives a strong peak at 268 nm, which is longer than the corresponding absorption of compound 1 at 244 nm. This band is known to be longitudinal polarized and is red-shifted with the size of polyacenes. The difference in the spectra of compounds 1 and 2 is readily understood by the size of their major chromophores, i.e. an anthracene moiety in compound 2 and a naphthalene in compound 1. A much weaker band of $^1$A→$^1$L$_a$ transition appears at 387 nm, also significantly red-shifted to the corresponding one of compound 1 at 300 nm. The latter band is partly overlapped with the $^1$A→$^1$L$_b$ transition at 324 nm.

Compound 2 is stable at ambient temperature, while it begins to decompose at about 128° C. and turns to purplish. The fragmentation temperature is a little lower than that of compound 1, which decomposes at 150° C. The thermal stability of compound 2 is slightly lower than 1. A 10% weight loss, as indicated in a thermogravimetric curve (FIG. 2), corresponds to the weight ratio of a CO unit. The pentacene thus produced is stable up to 300° C. Its UV spectrum shows a strong peak at 300 nm ($^1$B band for a π-π* transition), along with a characteristic long wavelength absorptions at 576 nm ($^1$L$_a$ band). The spectrum is identical to that obtained from authentic pentacene, indicating a very high yield for thermal transformation. In IR region, the strong absorption of carbonyl group at 1782 cm$^{-1}$ diminished completely after heating. The solubility of compound 2 is similar to that of compound 1, i.e. ~0.7 mg/mL in dichloromethane (DCM) and tetrahydrofuran (THF).

As to its photochemistry, compound 2 also exhibited salient photocolorant behavior. Upon ultraviolet irradiation at the absorption peak of ~366 nm in room temperature, degassed THF, compound 2 turned from colorless to purplish. Spectroscopically, as shown in FIG. 3A, with an increase of exposure time, a new absorption band with the peak wavelength around 575 nm gradually increased. An isosbestic point was observed at ~395 nm throughout the photolysis, indicating the existence of only two moieties in THF, the reactant compound 2 and product. Since the spectral feature of the new band, including the vibronic progression and the associated peak wavelengths, is identical with that of pentacene (Cf. FIGS. 1 and 3), the CO expulsion from compound 2 upon UV excitation to form pentacene is well justified. Note the UV induced compound 2→pentacene reaction has to be performed free from $O_2$. Under aeration, instead of the pentacene formation, fragmentation occurred, as indicated by the resulting broad, diffusive absorption band of <400 nm upon photolysis in the aerated solution (not shown here).

The yield of photo-product, i.e. pentacene, was further analyzed in a more quantitative manner. In a prototypical experiment, after using a 10 mW/cm$^2$ 385 nm Nd:YAG pumped Ti$^{3+}$:Sapphire laser (LOTIS TII, LT-2211) to illuminate the 3 mL solution containing compound 2 (~1.2×10$^{-4}$ M in THF) under vigorous stirring for 40 sec, it was observed that the absorbance at 575 nm increased from near zero to ~0.43, corresponding to an increase of ~4.3×10$^{-5}$ M of pentacene. By taking the ratio of the number of pentacene being produced versus number of photon being absorbed by compound 2, the yield of pentacene production was then calculated to be 16.2±1.0%. In fact, as depicted in FIG. 3B, similar photochemistry takes place in compound 1 upon 310 nm irradiation in degassed THF, the result of which was previously unrecognized. Based on the similar photolysis protocol, the yield of pentacene from compound 1 was estimated to be 12.6±0.6%, which is significantly lower than the results for compound 2.

OTFT devices were also fabricated using a heavily n-doped Si wafer as the substrate and the gate, and SiO$_2$ was thermally grown to 2000 Å as a gate insulator. On top of the SiO$_2$, gold was deposited lithographically to 30 nm as the source and drain electrodes. Compound 2 was spin-coated repeatedly over the structure to form a thin film, which was then heated to produce pentacene. The output characteristics of a device with channel width 20 cm and length 10 μm exhibited typical FET characteristics. The OTFT operates in the p-type enhancement mode and exhibits a hard saturation. A plot of drain current ($I_D$) versus drain-source voltage ($V_{DS}$) at various gate voltages ($V_{GS}$) is shown in FIG. 4. The corresponding transfer characteristics, i.e. log($I_D$) vs. $V_{GS}$ for $V_{DS}$=−80V, and $\sqrt{I_D}$ vs. $V_{GS}$ in the saturation mode is shown in FIG. 5. The OTFT exhibits an on/off current ratio of about 1.82× 10$^4$, and the apparent field-effect mobility μ is estimated to be 1.2×10$^{-3}$ cm$^2$ V$^{-1}$ s$^{-1}$. Due to the limited solubility of compound 2, the thin films prepared by spin-coating process were not entirely contiguous. Since the pentacene did not cover the whole area between the source and the drain, the actual mobility shall be higher.

In summary, a new stable and soluble pentacene precursor 2 was synthesized in 40% yield from the cycloaddition of a furan derivative 3 and a benzonorbornadiene 4. Compound 2 releases a unit of CO upon heating at 128° C. or by irradiation with UV light (366 nm) to produce pentacene in nearly quantitative yield. Thin films of pentacene were prepared by spin-coating followed by thermal annealing, and found to display typical FET characteristics.

In addition, synthesis of dicarbonyl compound 12 may be performed according to the present disclosure. Compound 12 is stable at low temperature for a long period of time, and exhibits a higher solubility than either compound 1 or 2. Compound 12 is suitable for making thin films by spin-coating process, and can generate pure pentacene by heating and/or by the irradiation of UV light. At ambient temperature in organic solvent compound 12 loses one unit of CO slowly to yield the corresponding monocarbonyl compound 2.

The synthesis of compound 12 can be depicted in the following Scheme 1B. The first step was a cycloaddition between dichlorobenzoquinone A and 8-dimethylisobenzofulvene. An elimination of HCl was followed to give an orange-colored chloroquinone B in 93% yield. In this reaction the 8-dimethylisobenzofulvene was generated in situ by reacting benzo(7-isopropylidene)norbornadiene with 3,6-di (2'-pyridyl)-s-tetrazine. This reaction sequence can be repeated once again to fuse another moiety of 8-dimethyl-isobenzofulvene to give compound C in 85% yield. Compound C existed in a mixture of syn and anti isomers. Reductive aromatization of the central ring of C was achieved by reacting with sodium borohydride, while D was obtained in 92% yield. Compound E was obtained by the esterification of D to a ditriflate (70%) with trifluoromethanesulfonic anhydride, followed by a palladium-catalyzed reduction with formic acid. A final oxidation of E with ozone in dichloromethane at −78° C. cleaved the C=C double bonds successfully in 90% yield. The carbonyl groups of 12 showed a strong absorption in IR at 1793 cm$^{-1}$, and in $^{13}$C NMR a signal at δ 188.5. The total yield from A to 12 was about 37%.

Scheme 1B

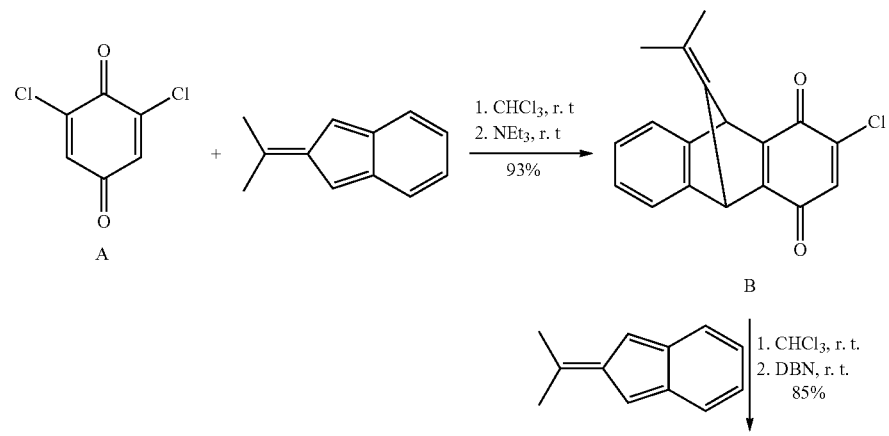

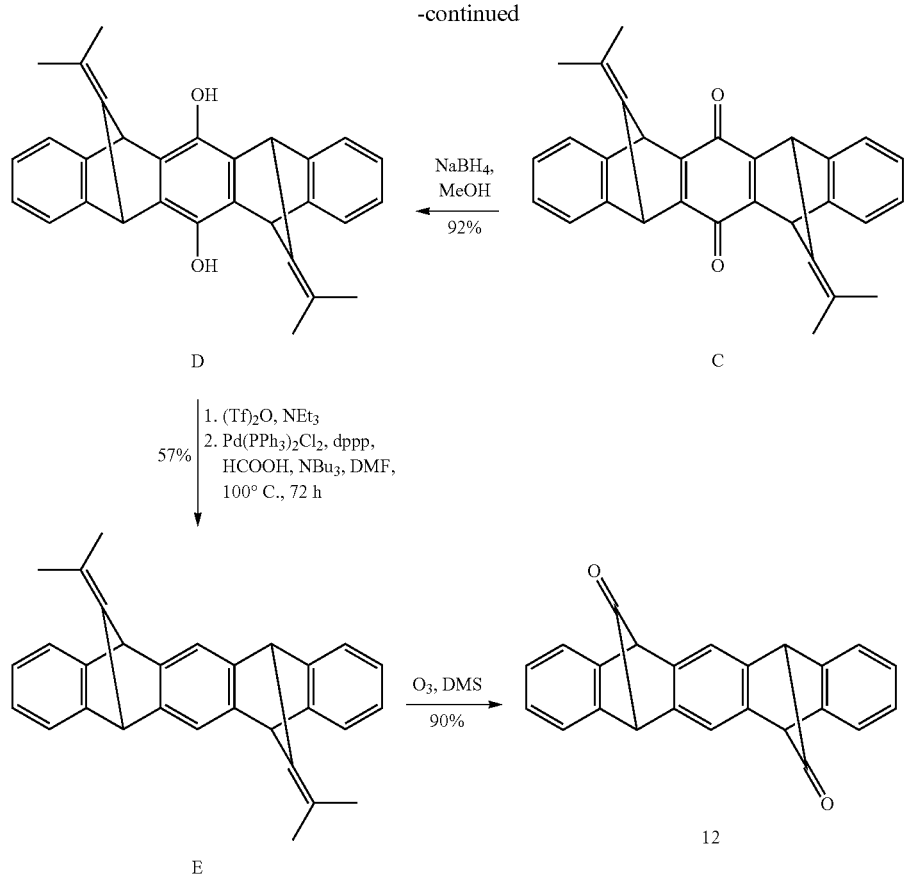

Synthesis of compound B in Scheme 1B. To a solution of compound A (177 mg, 1.00 mmol) and benzo(7-isopropylidene)norbornadiene (182 mg, 1.00 mmol) in chloroform (5 mL) was added slowly 3,6-di(2'-pyridyl)-s-tetrazine (236 mg, 1.00 mmol) at room temperature with stirring. The resulting solution was stirred for three hours, to it then was added triethylamine (0.40 mL, 3.0 mmol) and the mixture was stirred with a magnetic bar for another two hours. The mixture was washed with dilute sulfuric acid (3×10 ml, 5%), water and brine successively in an ice both. The organic solution was evaporated in vacuo, while a dark brown oil of compound B (275 mg, 93%) was collected. Mp 199-200° C.; $^1$H NMR (400 MHz, CDCl$_3$): δ 7.35 (m, 2H), 7.01 (m, 2H), 6.75 (s, 1H), 4.96 (d, J=1.6 Hz, 1H), 4.91 (s, 1H); $^{13}$C NMR (100 MHz, CDCl$_3$): δ 180.9, 175.3, 158.8, 158.4, 157.7, 146.9, 146.8, 143.2, 132.5, 125.7, 122.4, 122.3, 109.3, 49.5, 49.1, 19.0.

Synthesis of compound C in Scheme 1B. A crude product of B (296 mg, 1.00 mmol) was treated with benzo(7-isopropylidene)norbornadiene (182 mg, 1.00 mmol) and 3,6-di(2'-pyridyl)-s-tetrazine (236 mg, 1.00 mmol) according to the same procedure as the previous step. For the base catalyzed elimination, DBN (0.25 mL, 2.0 mmol) was used instead of triethylamine. Product C was purified by silica gel chromatograph eluted with hexane/ethyl acetate (5:1) to form orange solids (354 mg, 85%) as a mixture of anti and syn isomers. Mp 280-282° C.; $^1$H NMR (400 MHz, CDCl$_3$): δ 7.34 (dd, J=5.2, 3.2 Hz, 4H), 7.27 (dd, J=5.2, 3.2 Hz, 4H), 7.00 (dd, J=5.2, 3.2 Hz, 4H), 6.93 (dd, J=5.2, 3.2 Hz, 4H), 4.83 (s, 4H), 4.82 (s, 4H), 1.56 (s, 12H), 1.52 (s, 12H); $^{13}$C NMR (100 MHz, CDCl$_3$): δ 179.4, 159.0, 158.8, 157.0, 156.9, 147.6, 147.2, 125.4, 122.1, 108.2, 107.8, 48.8, 18.9, 18.8; MS (EI$^+$) m/z 416 (M$^+$, 100%), 401 (50), 392 (34), 300 (68); HRMS (m/z) calcd for C$_{30}$H$_{24}$O$_2$ 416.1779. Found: 416.1776.

Synthesis of compound D in Scheme 1B. To a round bottom flask containing compound C (416 mg, 1.00 mmol) in a mixed solvents of methanol (5 mL) and THF (2 mL) at 0° C. was added NaBH$_4$ (0.15 g, 4.0 mmol) slowly to avoid abrupt generation of hydrogen gas. After the addition the mixture was stirred at 0° C. for another two hours, and then was quenched by the addition of water (5 mL). The mixture was evaporated in vacuo and was extracted with dichloromethane (30 mL). The organic layer was dried over anhydrous MgSO$_4$, filtered, and concentrated in vacuo again. The residue was purified by a flash chromatograph eluted with hexane/dichloromethane (1:2) to give colorless solids of compound D (385 mg, 92%). $^1$H NMR (400 MHz, CDCl$_3$): δ 7.27 (dd, J=5.2, 3.2 Hz, 4H), 7.20 (dd, J=5.2, 3.2 Hz, 4H), 6.93 (dd, J=5.2, 3.2 Hz, 4H), 6.87 (dd, J=5.2, 3.2 Hz, 4H), 4.84 (s, 4H), 4.82 (s, 4H); MS (EI$^+$) m/z 418 (M$^+$, 100%), 403 (35), 390 (20); HRMS (m/z) calcd for C$_{30}$H$_{26}$O$_2$ 418.1935. Found: 418.1933.

Synthesis of compound E in Scheme 1B. To a solution of compound D (418 mg, 1.00 mmol) and triethylamine (2 mL) in chloroform (20 mL) was added trifluoromethanesulfonic anhydride (1.08 g, 3.8 mmol) dropwise with stirring at 0° C. After the addition was completed, the mixture was warmed up to room temperature and stirred for further 30 min. The reaction mixture was poured into ice-water (40 mL), and was extracted with ether. The organic layer was washed with aqueous HCl (2×20 mL, 1M), dried over MgSO$_4$, and concentrated in vacuo. The residue was purified by a silica gel column chromatograph eluted with hexane/dichloromethane (5:1). A triflate derivative of D was obtained (478 mg, 70%) as white solid. $^1$H NMR (400 MHz, CDCl$_3$): δ 7.36 (dd, J=5.2, 3.2 Hz, 4H), 7.27 (dd, J=5.2, 3.2 Hz, 4H), 7.03 (dd, J=5.2, 3.2 Hz, 4H), 6.96 (dd, J=5.2, 3.2 Hz, 4H), 4.97 (s, 4H), 4.94 (s, 4H), 1.60 (s, 12H), 1.53 (s, 12H); $^{13}$C NMR (100 MHz, CDCl$_3$): δ 157.5, 157.2, 147.4, 147.1, 143.1, 135.3, 135.1, 125.8, 125.8, 123.5, 122.2, 122.1, 120.3, 117.1, 114.0, 110.3, 110.0, 49.8, 19.1, 19.0; MS (EI$^+$) m/z 682 (M$^+$, 100%), 601 (18); HRMS (m/z) calcd for C$_{32}$H$_{24}$O$_6$ 682.0928. Found: 682.0919.

The triflate compound (682 mg, 1.00 mmol) was mixed with 1,3-bis(diphenylphosphino)propane (0.16 g, 0.38 mmol), bis(triphenylphosphino)palladium(II) chloride (0.10 g, 0.15 mmol), formic acid (1.0 mL) in dimethyl formamide (10 mL), and tri-n-butylamine (2.5 mL) together. It was stirred with a magnetic bar at 110° C. under a nitrogen atmosphere for 72 hours. After addition of aqueous HCl (30 mL, 1.5 M), the mixture was extracted with dichloromethane (2×30 mL). The combined organic layers were washed with aqueous HCl (2×30 mL, 1 M), dried over MgSO$_4$, and concentrated in vacuo. The yellow residue was purified by a silica gel column chromatograph eluted with hexane/dichloromethane (3:1) to yield compound E as colorless solids (274 mg, 82%). $^1$H NMR (400 MHz, CDCl$_3$): δ 7.22 (m, 6H), 6.90 (dd, J=5.2, 3.2 Hz, 4H), 4.61 (s, 4H), 1.50 (s, 12H); MS (EI$^+$) m/z 386 (M$^+$, 100%), 371 (42); HRMS (m/z) calcd for C$_{30}$H$_{26}$ 386.2029. Found: 386.2035.

Synthesis of compound 12 in Scheme 1B. A two-necked flash fitted with a glass tube to admit ozone, and a CaCl$_2$ drying tube was charged with compound E (1.00 g, 1.30 mmole) in anhydrous dichloromethane (30 mL). The flask was cooled to −78° C., and ozone was bubbled through the solution with stirring. The stream of ozone was stopped as soon as the solution turned bluish. Nitrogen gas was passed through the solution until the blue color was discharged. To the resulting solution was added dimethyl sulfide (1.0 mL, 1.3 mmol) at −55° C., and was stirred for six hours. The mixture was concentrated in vacuo at 0° C. and products were separated quickly by a silica gel chromatograph maintained at −10° C. eluted with hexane/dichloromethane (1:2). Compound 12 (274 mg, 82%) was obtained as pale yellow solids which can be kept at −10° C. for an extended period of time. $^1$H NMR (400 MHz, CDCl$_3$): δ 7.59 (s, 2H), 7.37 (dd, J=5.2, 3.2 Hz, 4H), 7.10 (dd, J=5.2, 3.2 Hz, 4H), 4.77 (s, 4H); $^{13}$C NMR (125 MHz, CDCl$_3$): δ 188.5, 139.6, 138.7, 126.8, 122.2, 116.9, 57.4; IR (CH$_2$Cl$_2$): 3006 (w), 1793 (s), 1437 (w), 1165 (w) cm$^{-1}$; MS (FAB$^+$) m/z 335 ((M+H)$^+$, 22.8%), 307 (100); HRMS (m/z) calcd for C$_{30}$H$_{25}$O$_2$ 335.1071. Found: 335.1072.

Pentacene and CO Adducts.

The following CO-adducts of pentacene are potential precursors for the generation of pure pentacene. The synthetic sequence of compound 13 can be depicted in Scheme 2, in which the second step (a reduction) was performed using sodium borohydride treatment and treatment with phosphorus chloride oxide in pyridine (Py).

Pentacene derivatives with carbonyl bridges include six types, i.e., types 1, 2, and 11-14. Types 1, 2, and 11 each possess one carbonyl bridge; types 12-13 each possess two carbonyl bridges, and type 14 possesses three carbonyl bridges. Structures of types 12-13 include both syn and anti geometrical isomers (syn isomers are shown), and those of type 14 include any possible syn/anti geometry (the syn-anti-syn isomer is shown).

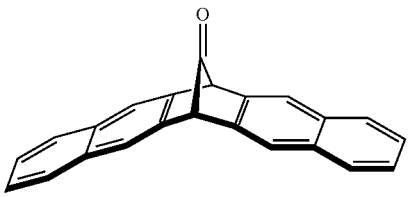

1

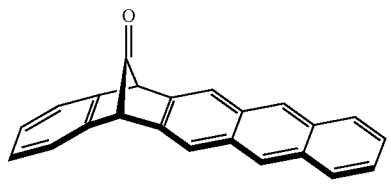

2

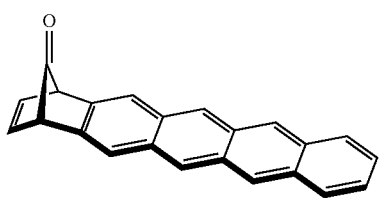

11

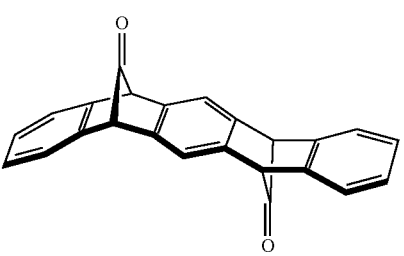

12

(syn and anti isomers)

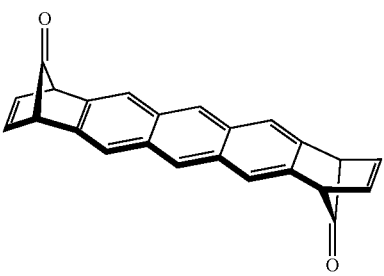

13

(syn and anti isomers)

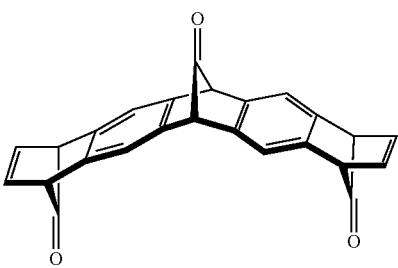

14

(syn and anti isomers)

In each compound of types 1, 2, and 11-14, there are 14 possible substituents, as indicated by R$_1$~R$_9$ in a general formula (A). In this formulae X denotes a possible carbonyl bridge (—C(=O)—) across each of the six-member ring. There exists at least one carbonyl bridge, but not necessarily all of them. Groups R$_1$~R$_9$ denote substituents, where R$_1$~R$_8$ can be hydrogen, methyl, cyano, methoxy, phenyl, fluoro, chloro, bromo atoms or groups; and $R_9$ can be hydrogen atom or trimethylsilylalkynyl group. Specific examples are given as groups 1~28 in Table 1.

TABLE 1

(Formula A)

Substituents for pentacene derivatives as indicated in general formula A, B, C, and D.

| No | $R_1$ | $R_2$ | $R_3$ | $R_4$ | $R_5$ | $R_6$ | $R_7$ | $R_8$ | $R_9$ |
|---|---|---|---|---|---|---|---|---|---|
| 1 | $CH_3$ | $CH_3$ | H | H | H | H | H | H | H |
| 2 | $CH_3$ | H | $CH_3$ | H | H | H | H | H | H |
| 3 | $CH_3$ | $CH_3$ | $CH_3$ | $CH_3$ | H | H | H | H | H |
| 4 | $CH_3$ | $CH_3$ | $CH_3$ | $CH_3$ | $CH_3$ | $CH_3$ | H | H | H |
| 5 | Cl | Cl | H | H | H | H | H | H | H |
| 6 | Cl | H | Cl | H | H | H | H | H | H |
| 7 | Cl | Cl | H | H | Cl | H | H | H | H |
| 8 | Cl | Cl | Cl | Cl | H | H | H | H | H |
| 9 | Cl | Cl | Cl | Cl | Cl | H | H | H | H |
| 10 | Cl | Cl | Cl | Cl | Cl | Cl | H | H | H |
| 11 | F | F | H | H | H | H | H | H | H |
| 12 | F | H | F | H | H | H | H | H | H |
| 13 | F | F | H | H | F | H | H | H | H |
| 14 | F | F | F | F | H | H | H | H | H |
| 15 | F | F | F | F | F | H | H | H | H |
| 16 | F | F | F | F | F | F | H | H | H |
| 17 | F | F | F | F | F | F | F | F | H |
| 18 | F | F | F | F | F | F | F | F | F |
| 19 | CN | CN | H | H | H | H | H | H | H |
| 20 | CN | H | CN | H | H | H | H | H | H |
| 21 | CN | CN | CN | CN | H | H | H | H | H |
| 22 | $OCH_3$ | $OCH_3$ | H | H | H | H | H | H | H |
| 23 | $OCH_3$ | H | $OCH_3$ | H | H | H | H | H | H |
| 24 | $OCH_3$ | $OCH_3$ | $OCH_3$ | $OCH_3$ | H | H | H | H | H |
| 25 | $OCH_3$ | H | CN | H | H | H | H | H | H |
| 26 | $OCH_3$ | $OCH_3$ | CN | CN | H | H | H | H | H |
| 27 | Ph | H | Ph | H | H | H | H | H | H |
| 28 | H | H | H | H | H | H | H | H | —C≡C—Si(CH$_3$)$_3$ |

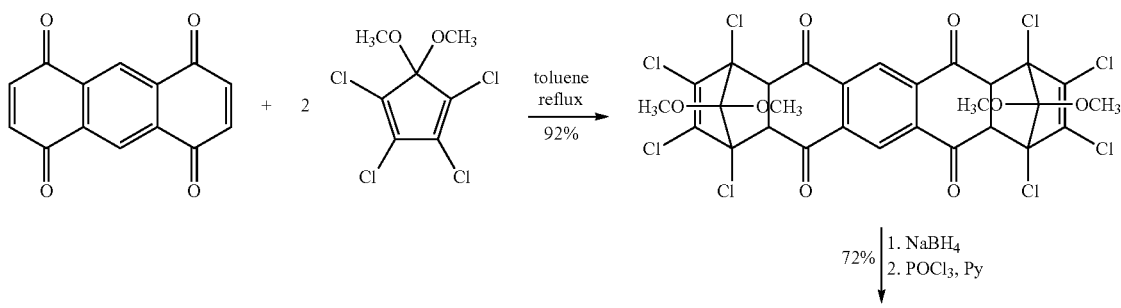

Scheme 2

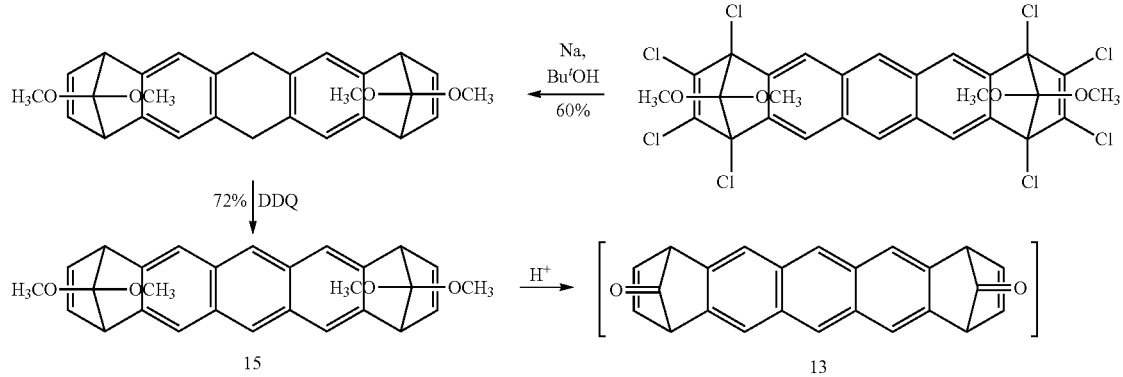

Pentacene can be generated from the dimethyl ketal 15 in acid as evidenced by the absorption spectra shown in FIG. 6. The intermediate diketone 13 cannot be isolated at ambient temperature, yet it can be trapped at a lower temperature. The octachloro-substituted derivatives can be used to yield 1,2,3,4,8,9,10,11-octachloropentacene in a similar way (see FIG. 7). As some fluorinated pentacene derivatives do exhibit FET characteristics, the halogenated analogues are also of potential usefulness for OTFT.

Ketals that can Release $CO_2$ and Ethylene.

The thermal stability of compounds 11, 13, and 14 are relatively low, due to the location of CO bridges at the edges of the polycycles. Thermal fragmentation of the corresponding ethylene ketals, e.g., compound 16, can be achieved directly without going through the ketone derivatives. The solubility of these ketals in organic solvents are substantially higher than the corresponding ketones, however, the thermal decomposition temperature is comparatively higher. Nevertheless, the yield of pentacene is good, and the film thus produced exhibits typical FET characteristics. A single crystal X-ray diffraction structure of 13 is shown in FIG. 8. The thermogravimetric analysis (TGA) plot (FIG. 9) indicates that the fragmentation happens at about 225° C.

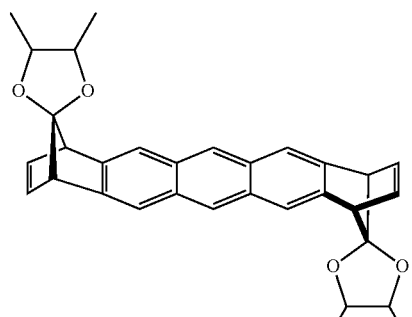

17

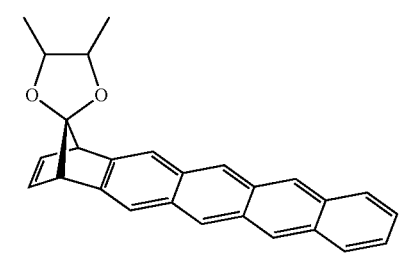

18

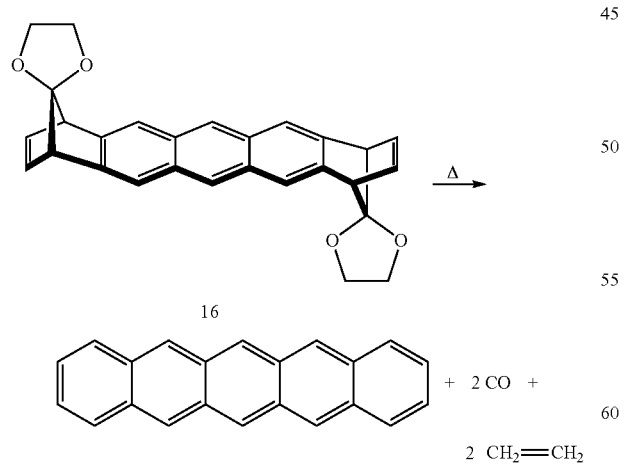

Spiroketals with methyl substituents, e.g., 2,3-butandiol ketal-bridged precursor compounds such as 17 and 18, can offer lower fragmentation temperatures.

Pentacene derivatives with ketal bridges include six types, i.e., types, numbered below as compounds VII~XII. Types VII~IX each possess one ketal bridge, types X~XI each possess two ketal bridges, and type XII possesses three ketal bridge. Structures of types X~XII include both syn and anti geometrical isomers.

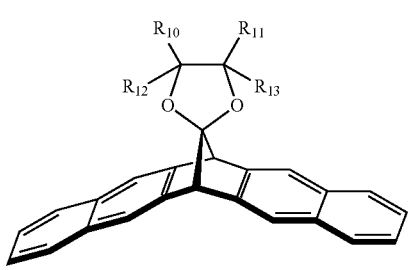

VII

VIII

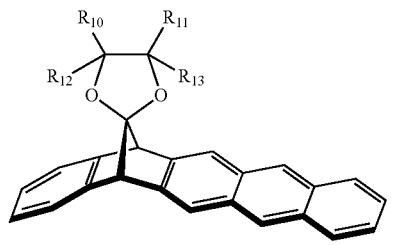

IX

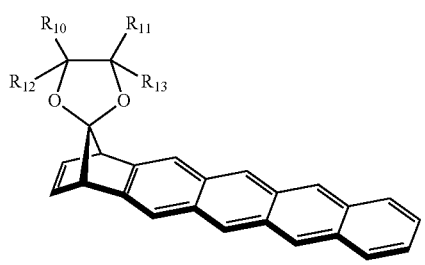

X

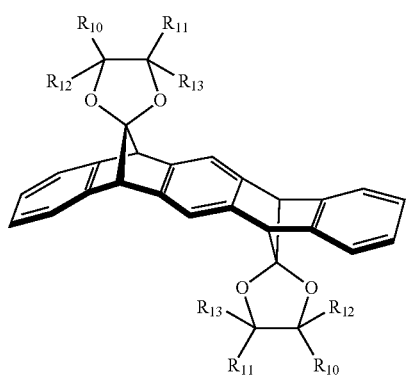

(syn and anti isomers)

XI

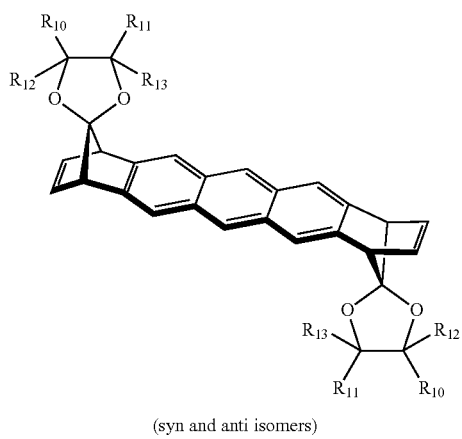

(syn and anti isomers)

XII

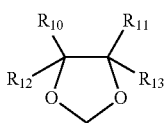
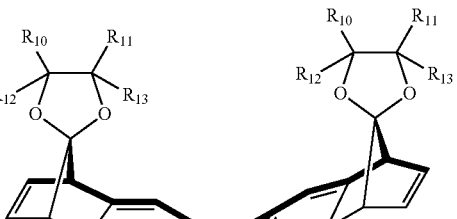

(syn and anti isomers)

$R_{10}$~$R_{13}$ denote the substituents in each ketal bridging groups in the structures VII~XII, where they can be hydrogen, methyl, ethyl, propyl, butyl, pentyl, hexyl, cyano, methoxy, phenyl, chloro, atoms or groups. $R_{10}$~$R_{11}$ can also be a part of a ring as shown in the following form, where $R_{10}$~$R_{11}$ are expressed as —CH=CH—CH=CH—. In Table 2 it shows some examples (29~42) for the ketal substituents $R_{10}$~$R_{13}$.

TABLE 2

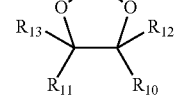

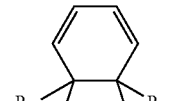

Substituents for pentacene derivatives as indicated in the ketal types VII~XII.

| No | $R_{10}$ | $R_{11}$ | $R_{12}$ | $R_{13}$ |
|---|---|---|---|---|
| 29 | H | H | H | H |
| 30 | CH₃ | H | H | H |
| 31 | CH₃ | CH₃ | H | H |
| 32 | CH₃ | CH₃ | CH₃ | H |
| 33 | CH₃ | CH₃ | CH₃ | CH₃ |
| 34 | CH₃ | C₂H₆ | H | H |
| 35 | CH₃ | CH₂CH₂CH₃ | H | H |
| 36 | CH₃ | CH₂CH₂CH₂CH₃ | H | H |
| 37 | C₂H₆ | C₂H₆ | H | H |
| 38 | CH₂CH₂CH₂CH₃ | H | H | H |
| 39 | CH₂CH₂CH₂CH₂CH₃ | H | H | H |
| 40 | Ph | H | H | H |
| 41 | —CH=CH—CH=CH— | | H | H |
| 42 | —CH=CH—CH=CH— | | CH₃ | CH₃ |

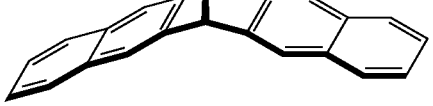

In each compound of types VII~XII, there are 14 possible substituents, as indicated by $R_1$~$R_9$ in a general formula. In this formulae Y denotes a possible ketal bridge (—OC($R_{10}R_{11}$)C($R_{12}R_{13}$)O—) across each of the six-member ring. There exists at least one ketal bridge, but not necessarily all of them. Groups $R_1$~$R_9$ denote alkyl substituents, where $R_1$~$R_8$ can be hydrogen, methyl, cyano, methoxy, phenyl, fluoro, chloro, bromo atoms or groups; and $R_9$ can be hydrogen atom or trimethylsilylalkynyl group. Specific examples are given as groups 1~28 in Table 1.

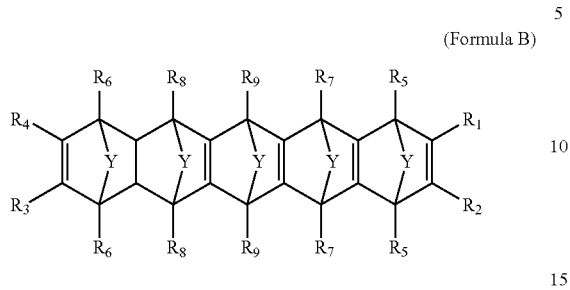

(Formula B)

Depicted below is the rational design of a series of pentacene CO adducts 1, 2, and 11-14, among which syntheses of 1 and 2, and their physical properties have been elaborated in separated reports. See K.-Y. Chen, H.-H. Hsieh, C.-C. Wu, J.-J. Hwang, T. J. Chow, *Chem. Commun.* 2007, 1065; H.-H. Huang, H.-H. Hsieh, C.-C. Wu, C.-C. Lin, P.-T. Chou, T.-H. Chuang, Y.-S. Wen, T. J. Chow, *Tetrahedron Lett.* (2008), 49, 4494; and T.-H. Chuang, H.-H. Hsieh, C.-K. Chen, C. C. Wu, C. C. Lin, P.-T. Chou, T.-H. Chao, T. J. Chow, *Org. Lett.* (2008), 10, 2869; which are hereby incorporated by reference. Compounds 1 and 2 have successfully produced pure pentacene upon heating at 150 and 128° C., respectively. Ibid. The pentacene films thus produced exhibited typical OTFT characteristics, i.e. a device made of compound 1 displayed an on/off current ratio about $1.2 \times 10^5$ and field-effect mobility ($\mu$) ca. 0.01 $cm^2 V^{-1} s^{-1}$. Moreover, for both compounds 1 and 2, it has also been shown that the CO expulsion can be achieved with the irradiation of light and may thus be feasible to produce the pentacene films under ambient temperature to minimize the temperature-dependent annealing process.

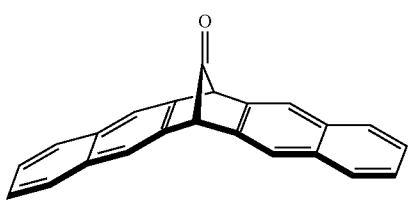

1

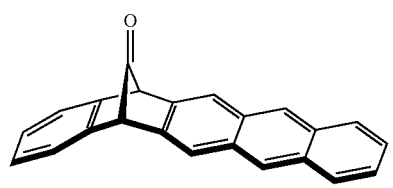

2

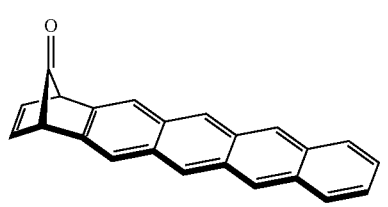

11

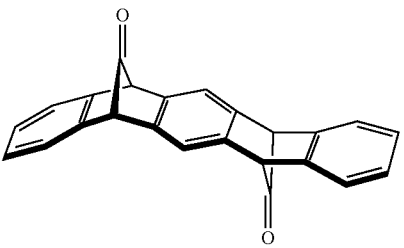

12A

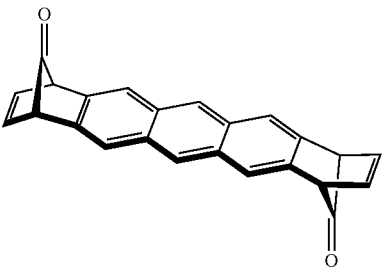

13A

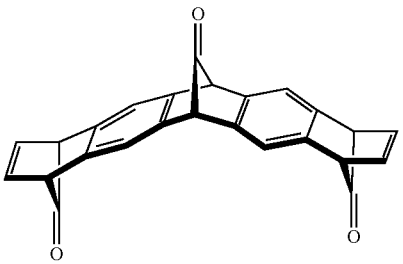

14A

Yet the solubility of compound 1 of ~0.7 mg/mL in methylene chloride or THF is not quite satisfactory, such that casting processes have to be repeated several times in order to accumulate sufficient materials to prepare a film with required thickness. Likewise, while the solubility of compound 2 is better than compound 1, it is not believed to be sufficiently soluble so as to prepare useful films in a single casting. Thus, still further improvements are presented below.

A pathway for the synthesis of compound 13A (i.e. anti-13) is depicted in Scheme 3. The pentacene skeleton of 22 can be assembled by double annulations of anthradiquinone 20 and 2,3,4,5-tetrachloro-1,1-dimethoxycyclopentadiene 21. A mixture of syn and anti isomers was obtained as yellow solids after being purified by column chromatograph, while the mixture was subjected to the next synthetic step. Aromatization of the central anthracene moiety was accomplished by a reduction/dehydration sequence, i.e., by reducing the carbonyl groups to hydroxyls with sodium borohydride, followed by the dehydration with phosphoryl chloride in the presence of pyridine. The syn and anti isomers of compound 23 were separated at this stage, and the geometry of anti-isomer was solved by X-ray crystallography. The three aromatic $^1$H NMR signals of anti-23 appeared at $\delta$ 7.26, 7.87, and 8.32. The overall yield of 23 (two isomers) from 20 was about 65%. Compound 23 can be used for the preparation of 1,2,3,4,8,9, 10,11-octachloropentacene 26, which has been predicted as a potential n-type FET gate material according to Chen et al., *ChemPhysChem* 2006, 7, 2003. The chlorine atoms were then stripped off by a reduction of sodium in the presence of t-butanol. However, under such a condition the central aromatic ring was also reduced, forming compound 24. The aromaticity can be regenerated by an oxidation with dichlorodicyanoquinone (DDQ). The $^1$H NMR spectrum of 25 is similar to that of 23, whereas the hydrogen atoms on the double bonds appear at δ 6.75. The overall yield of 5-step synthetic routes from 20 to 25 was about 45%.

shift for the latter. The weak of $^1A \rightarrow {}^1L_a$ bands of both 23 and 25 at 300-380 nm nearly overlapped with each other. After acidic hydrolysis, the standard pentacene absorption pattern

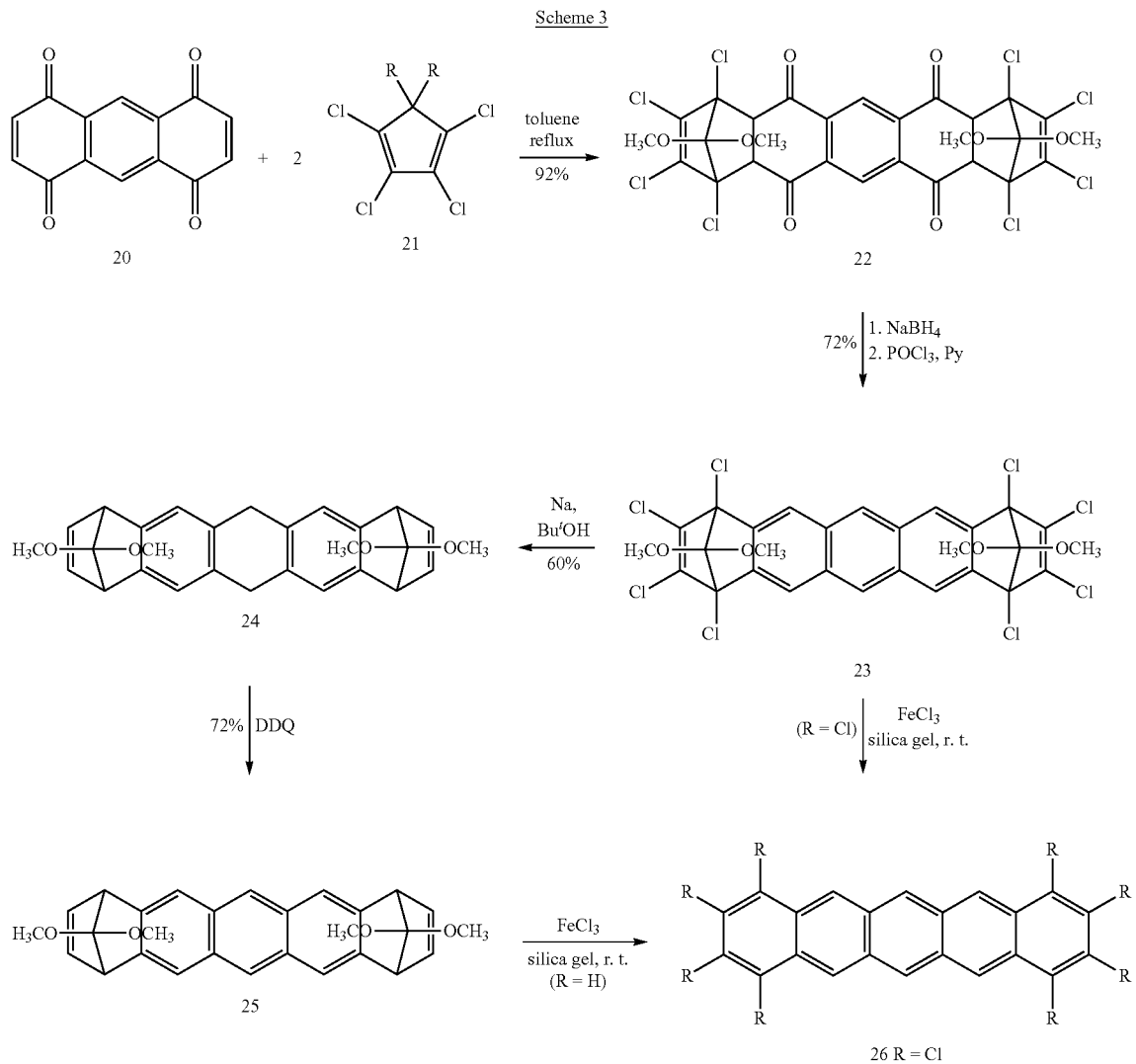

Scheme 3

Hydrolysis of the ketal groups of 25 in an attempt to collect diketone 13A by standard methods in acidic solutions unfortunately failed. Instead, a complex mixture resulted, probably due to the labile nature of 13A, which decomposed readily at ambient conditions. Pentacene could be obtained directly, however, when ketal 25 was treated with a heterogeneous mixture of ferric trichloride and silica gel in dichloromethane. Pure pentacene can thus be obtained after filtering off the solids and dried. A similar hydrolysis can also be applied to octachloride 23 to yield octachloropentacene 26 as a dark purple solid.

The transformation can be well elaborated via the absorption spectra depicted in FIG. 16. A distinctive strong absorption appeared at 240-320 nm is attributed to the $^1A \rightarrow {}^1B$ transition of aromatic chromophore of each pentacene derivative. For a fair comparison, the spectrum of compound 1 (green line) and compound 2 (brown line) at shorter wavelengths are plotted in FIG. 16. The spectra of 23 (red line) and 25 (blue line) are located close to each other, with a slight blue can be clearly identified by both the strong $^1B$ band and a very characteristic $^1L_a$ band. The $^1B$ band of pentacene appears at 300 nm (black line), and that of 26 at 318 nm (pink line). The long wavelength $^1L_a$ band of pentacene is located at 496-576 nm with characteristic vibronic progressions. The corresponding band of octachloropentacene is at 477-595 nm, again slightly red shifted with respect to that of pentacene (inset in FIG. 16).

A slight modification of the ketal structures of 25 resulted in pentacene in good yield. As shown in 25e, the ethylene ketal moieties dissociate into ethylene and carbon dioxide at an elevated temperature. The TGA curve (red line) indicated that the dissociation started at 215° C., while the percentage of weight loss corresponds properly to the calculated value of ethylene along with carbon dioxide. The formation of pentacene was confirmed by its absorption spectrum, which was identical to an authentic sample. An analogous fragmentation was also found for the octachloride derivative 23e, while octachloropentacene 26 was obtained by heating at 285° C.

The reaction proceeds quite cleanly according to the weight ratio in TGA profile, as shown in FIG. 17 (blue line).

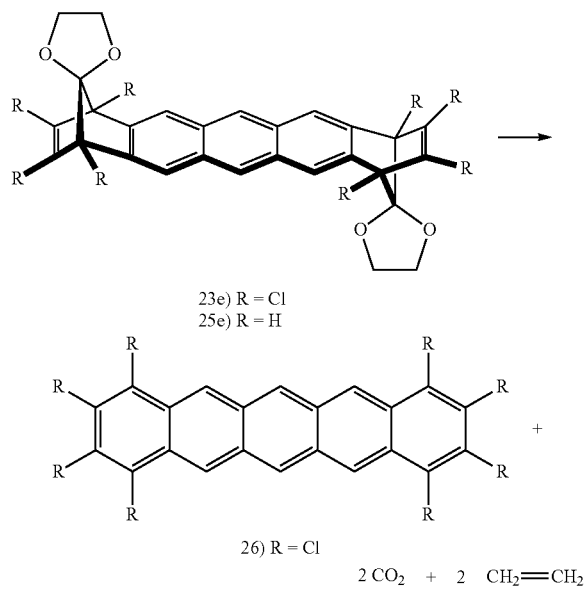

23e) R = Cl
25e) R = H

26) R = Cl $2 CO_2 + 2 CH_2\!\!=\!\!CH_2$

An OTFT device was made by spin-coating a toluene solution of 25e on the surface of a $SiO_2$ gate insulator. An amorphous thin film was formed after drying, and then was heated at 235° C. for 30 min to convert 25e to pentacene with a good conversion yield. The device exhibited typical FET characteristics even though the resulting film appeared thin. The output parameters were measured across a source-drain channel with 1 mm width and 5 μm length. Plot of drain current ($I_D$) versus drain-source voltage ($V_{DS}$) at various gate voltages ($V_{GS}$) is shown in FIG. 15A. The corresponding transfer characteristics, i.e. $\log(I_D)$ vs. $V_{GS}$ for $V_{DS}=-80$ V, and $\sqrt{I_D}$ vs. $V_{GS}$ in the saturation mode is shown in FIG. 15B. The OTFT exhibits an on/off current ratio about $1.7\times10^3$, and an apparent field-effect mobility (μ) about $7.89\times10^{-6}$ $cm^2$ $V^{-1}s^{-1}$. The relatively inferior performance of this device is attributable to the thinness of the pentacene film as mentioned above. The film quality should improve by suppressing the rate of pentacene vaporization, or by reducing the annealing temperature.

In summary, the conceptual design and synthesis of a series of soluble pentacene precursors have been accomplished. The doubly CO bridged compound 13A is not stable enough to sustain at ambient conditions. Upon acidic hydrolysis, the dimethyl ketal derivatives 23 and 25, yielded pentacenes without isolation of the corresponding ketones. Amorphous thin films can thus be prepared by spin-casting the solutions of 23 and 25 in toluene with good solubility; however, heating these films did not yield either pentacene or 1,2,3,4,8,9,10,11-octachloropentacene. A slight modification on 23 and 25 led to the corresponding ethylene ketals 23e and 25e. TGA analyses of the latter compounds indicated that they dissociated at 226 and 290° C., respectively, and generated pentacenes in high yields. OTFT device made of thin film of 23e exhibited typical FET characteristics.

D. Device Fabrication.

Solid films were made by spin-coating the solutions of precursor compounds. In some cases multiple spin-coating procedures may be applied in order to obtain a film of satisfactory thickness. After solvent was evaporated, a solid web-like film was formed (FIG. 10 shows a film made of compound 1). Heating the film at an elevated temperature (e.g. 150° C. for compound 1, 128° C. for compound 2, and 230° C. for compound 25e) initiated a fragmentation reaction, thus produced a web-like film of pure pentacene as shown in FIG. 11 having purplish blue tint.

OTFT devices were made in a standard "bottom contact and bottom gate" manner with channel width 20 cm and length 10 μm were constructed which have pentacene films formed from compounds 1 and 2, as well as from compound 25e. See FIGS. 12A and 12B. Their characteristics are outlined in the graphs presented in FIGS. 13A and 13A (FET characteristics for device from compound 1), 14A and 14B (FET characteristics for device from compound 2), and 15A and 15B (FET characteristics for device from compound 25e).

The results demonstrated in FIGS. 12A-15B indicate that these precursor compounds are of value for the manufacture of OTFTs.

Experimental Details.

Melting points were taken on a Fargo MP-2D melting-point apparatus and were not corrected. UV spectra were recorded on a Hewlett-Packard 8453 spectrophotometer. Infrared spectra were measured on a Perkin-Elmer L118-F000 FT-IR spectrometer as either thin film or solid dispersion in KBr. Nuclear magnetic resonance spectra were recorded on Bruker AC300 and AV500 super-conducting FT NMR spectrometers with all chemical shifts reported in ppm from tetramethylsilane as an internal standard. Mass spectra were obtained on a Joel JMS 700 double focusing spectrometer. Elemental analyses were performed on a Perkin-Elmer 2400 elemental analyzer. Thermal gravimetric analyses were measured on a Perkin-Elmer Pyris 1 thermogravimetric analyzer. Differential scanning calorimetry was done on a Perkin-Elmer DCS-7 instrument. Column chromatography was carried out using 230-400 mesh silica gel.

(1) Synthesis of Dimethyl Ketal 23 and 25: Compound 22.

Anthrcene bisquinone (0.33 g, 1.40 mmole) and 1,1-dimethoxy-2,3,4,5-tetrachlorocyclopentadiene (1.10 g, 4.2 mmole) was dissolved in dry toluene under a nitrogen atmosphere. The mixture was heated to reflux for 4 days, then it was cooled to ambient temperature. The solution was filtered, and evaporated to dryness. The yellow solids were recrystallized from THF:hexane to give a mixture of anti and syn geometrical ⅓ isomers (0.77 g, 73%). $^1$H NMR (300 MHz, THF-d$_8$) signals assigned to anti isomer: δ 3.55 (s, 6H), 3.70 (s, 6H), 3.89 (s, 4H), 8.34 (s, 2H); signals assigned to syn isomer: δ 3.56 (s, 6H), 3.70 (s, 6H), 3.88 (2s, 4H), 8.39 (2s, 2H). $^{13}$C NMR (75 MHz, THF-d$_8$) signals assigned to anti isomer: δ 52.63, 53.36, 57.41, 78.72, 112.62, 126.26, 130.36, 139.68, 189.40; for syn isomer: δ 52.63, 53.36, 57.41, 78.72, 112.56, 126.56, 130.47, 139.68, 189.63. IR (KBr) for mixture: v 3519 (m), 3382 (m), 2984 (w), 2956 (w), 2848 (w), 1703 (s), 1601 (m), 1466 (m), 1260 (s), 1191 (s), 1133 (m), 1033 (m), 997 (s), 906 (w), 799 (w), 547 (w) $cm^{-1}$. MS (EI) m/z 726.88 ([M-Cl]$^+$, 44%). Analysis calculated for $C_{28}H_{18}O_8Cl_8$: C, 43.90; H, 2.37. Found: C, 43.77; H, 2.26

Compound 23.

Compound 22 (1.00 g, 1.31 mmole) was dissolved in methanol (15 mL) in a round bottom flask, which was immersed in a cold water bath. To it was added $NaBH_4$ (0.30 g, 8.0 mmole) slowly to avoid abrupt generation of large amount of hydrogen gas. After the addition the mixture was stirred at room temperature for another two hours, it was quenched by the addition of excess wet THF. The mixture was extracted with THF (50 mL×3), filtered, and evaporated in vacuo. The product 22-1 was crystallized with THF:hexane to give white solids (0.72 g, 71%) as an anti/syn mixture. $^1$H NMR (300 MHz, THF-d$_8$): δ 2.97 (s, 4H), 3.54 (s, 6H), 3.55 (s, 6H), 4.88 (d, J=9 Hz, 4H), 4.95 (d, J=9 Hz, 4H), 7.32 (s, 2H). $^{13}$C NMR (125 Mz, THF-d$_8$): δ 51.99, 53.08, 53.64, 67.61, 77.99, 116.71, 128.80, 130.19, 141.92. IR (KBr): v 3550 (m), 3477 (s), 3421 (s), 2984 (w), 2949 (w), 2904 (w), 2845 (w), 1638 (m), 1615 (s), 1451 (w), 1299 (w), 1213 (w), 1184 (s), 1121 (m), 1002 (s), 902 (w), 777 (w), 618 (m), 471 (w) cm$^{-1}$. Analysis calculated for C$_{28}$H$_{26}$O$_8$Cl$_8$: C, 43.44; H, 3.39. Found: C, 43.38; H, 3.27.

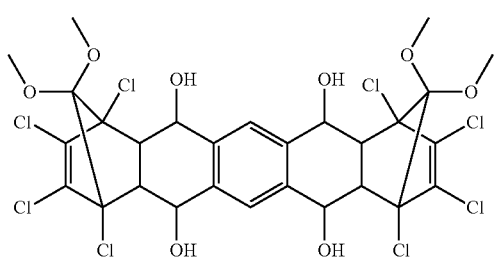

22-1

To a round bottom flask containing compound 22-1 (1.50 g, 1.94 mmole) in dry pyridine under a nitrogen atmosphere was injected POCl$_3$ (3.0 g, 20 mmole) gradually through a syringe pump. The mixture was heated at 60° C. for 30 hrs for the reaction to complete. It was then cooled to −78° C., and the reactants were quenched by the slow addition of water. The resulted mixture was extracted several times between CH$_2$Cl$_2$ and aqueous 20% HCl to remove pyridine. The organic solution was washed with saturated sodium bicarbonate, dried over anhydrous MgSO$_4$, filtered, and evaporated in vacuo. The solid residue was purified by silica gel chromatograph eluted with CH$_2$Cl$_2$:hexane to give both anti and syn forms of compound 23 (1.12 g, yield 82% for anti and syn combined). Decomposition temperatures for anti: 297° C., and for syn: 271° C. $^1$H NMR (400 MHz, CDCl$_3$) for anti form: δ 3.43 (s, 6H), 3.72 (s, 6H), 7.87 (s, 4H), 8.32 (s, 2H); and for syn form: δ 3.42 (s, 6H), 3.72 (s, 6H), 7.84 (s, 4H), 8.26 (s, 2H). $^{13}$C NMR (100 MHz, CDCl$_3$) for anti form: δ 52.42, 53.24, 78.55, 119.70, 121.89, 127.49, 131.21, 135.36, 138.62; and for syn form: δ 52.39, 53.22, 78.54, 119.67, 121.88, 127.40, 131.15, 135.35, 138.58. IR (KBr) for anti form: v 3540 (m), 3510 (m), 3465 (m), 3416 (m), 3236 (w), 3053 (w), 2979 (w), 2946 (m), 2841 (m), 1599 (m), 1457 (w), 1281 (w), 1195 (s), 1130 (m), 1099 (w), 1013 (m) cm$^{-1}$; for syn form: v 3542 (w), 3508 (w), 3488 (m), 3412 (m), 3234 (w), 2990 (w), 2949 (m), 2845 (w), 1638 (w), 1615 (w), 1598 (m), 1455 (w), 1280 (w), 1213 (m), 1191 (s), 1151 (m), 1129 (m), 1100 (m) cm$^{-1}$. MS (FAB$^+$) m/z 697.87 (M$^+$, 5%). Analysis calculated for C$_{28}$H$_{18}$O$_4$Cl$_8$ anti: C, 47.90; H, 2.58. Found: C, 48.06; H, 2.58; syn: C, 47.90; H, 2.58. Found: C, 47.86; H, 2.81.

Compound 25

A three-necked round bottom flask fitted with a refluxing condenser and a nitrogen inlet/outlet was charged with a mixture of anti and syn isomers of compound 23 (1.2 g, 1.7 mmole) in dry THF (30 mL) under a nitrogen atmosphere. To the flask was added fresh sodium (0.98 g, 43 mmole), followed by t-butanol (2.1 g, 28 mmole). The mixture was heated to reflux for 30 hr. It was then cooled and filtered. The filtrate was neutralized with saturated sodium bicarbonate, and was extracted several times with CH$_2$Cl$_2$. The organic layers were combined, dried over anhydrous MgSO$_4$, and evaporated in vacuo. A crude product of compound 24 was obtained, which was subjected to the next step without further purification.

A crude product of 24 obtained from previous step (0.20 g, 0.47 mmol) was dissolved in 1,4-dioxane (15 mL) under a nitrogen atmosphere. To it was added dichlorodicyanoquinone (430 mg, 1.9 mmol), and the mixture was heated to 60° C. for 24 hr. The crude product was poured into an aqueous solution of Na$_2$S$_2$O$_3$ (50 mL) and was stirred for a half hour. The mixture was extracted with CH$_2$Cl$_2$ several times, and the combined organic parts were dried over anhydrous MgSO$_4$, filtered, and evaporated in vacuo. The solid residue was purified by silica gel chromatograph eluted with CH$_2$Cl$_2$:hexane to yield 25 in 70% (0.14 g, 0.33 mmol). Decomposition temperatures for anti is 288° C. and for syn is 252° C. $^1$H NMR (300 MHz, CDCl$_3$) for anti: δ 3.11 (s, 6H), 3.31 (s, 6H), 4.09 (d, J=3 Hz, 4H), 6.66 (t, J=3 Hz, 4H), 7.66 (s, 4H), 8.08 (s, 2H); and for syn: δ 3.11 (s, 6H), 3.32 (s, 6H), 4.11 (d, J=3 Hz, 4H), 6.67 (t, J=3 Hz, 4H), 7.68 (s, 4H), 8.10 (s, 2H). $^{13}$C NMR (75 MHz, CDCl$_3$) for anti: δ 50.77, 52.02, 53.41, 119.53, 125.42, 126.66, 130.73, 137.92, 143.07; and for syn: δ 50.74, 52.01, 53.40, 119.51, 125.41, 126.65, 130.71, 137.88, 143.09. MS (EI) m/z 426.18 (M$^+$, 100%). Analysis calculated for C$_{28}$H$_{26}$O$_4$: C, 78.85; H, 6.14. Found: C, 78.47; H, 6.23.

(2) Synthesis of Ethylene Glycol Ketal 23e and 25e

The procedures for the preparations of ethylene glycol ketal 23e and 25e are basically the same as those for the preparation of 23e and 25e as depicted in the following scheme.

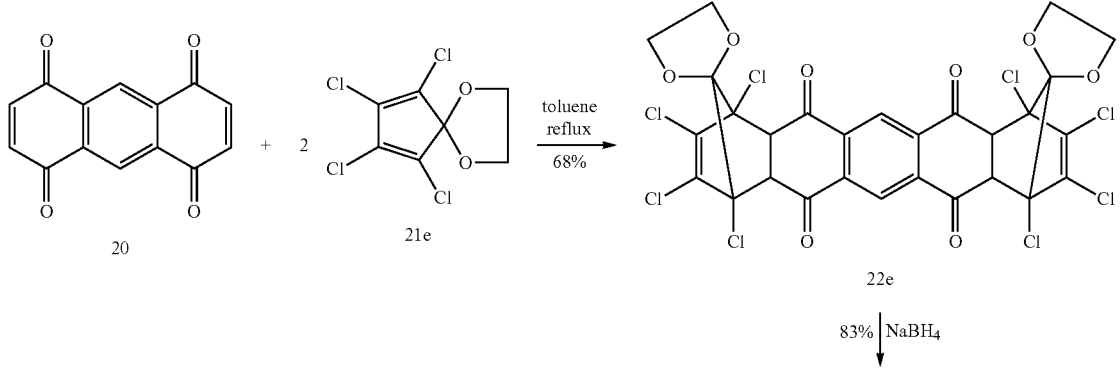

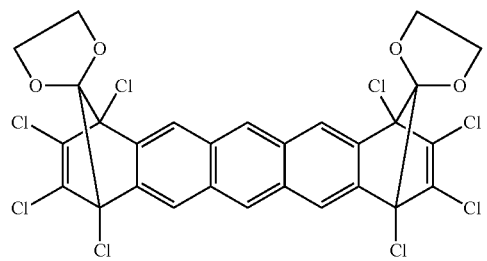 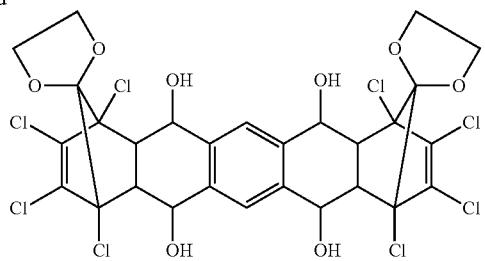

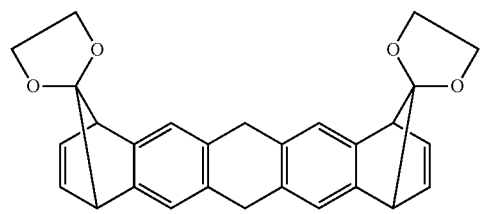 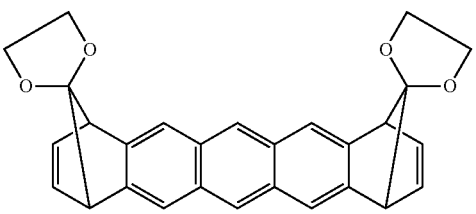

Compound 22e.

A similar procedure for the preparation of compound 22 was conducted. A combined yield of syn and anti isomers of 22e was 80%. $^1$H NMR (300 MHz, THF-d$_8$): δ 3.88 (s, 4H), 4.23 (t, J=6 Hz, 4H), 4.35 (t, J=6 Hz, 4H), 8.42 (s, 2H). $^{13}$C NMR (75 MHz, THF-d$_8$): δ 57.34, 68.20, 69.40, 77.48, 121.56, 126.69, 130.11, 139.69, 189.42. IR (KBr): ν 3603 (w), 3523 (m), 3442 (m), 3346 (m), 3208 (w), 2974 (w), 2908 (w), 1704 (s), 1628 (w), 1593 (s), 1532 (w), 1472 (w), 1417 (w), 1256 (s), 1215 (s), 1164 (w), 1122 (m), 1096 (w), 1027 (m), 1002 (m) cm$^{-1}$. MS (FAB$^+$): m/z 758.82 ((M+H)$^+$, 30%). Analysis calculated for C$_{28}$H$_{14}$O$_8$Cl$_8$: C, 44.13; H, 1.85. Found: C, 44.34; H, 2.28.

Compound 23e.

Compound 22e was first reduced by NaBH$_4$ to give 22e-1 according to the same procedure for the preparation of 22-1. The combined yield of syn and anti isomers of 22e-1 was 83%. $^1$H NMR (400 MHz, THF-d$_8$): δ 2.89 (s, 4H), 4.13 (t, J=6 Hz, 4H), 4.20 (t, J=6 Hz, 4H), 4.88 (d, J=8 Hz, 4H), 5.04 (d, J=8 Hz, 4H), 7.34 (s, 2H). $^{13}$C NMR (125 MHz, THF-d$_8$): δ 53.70, 67.25, 67.66, 68.89, 76.63, 125.28, 128.73, 129.78, 141.71. IR (KBr): ν 3663 (w), 3536 (w), 3416 (w), 3301 (s), 2934 (w), 2906 (m), 1660 (w), 1630 (w), 1601 (m), 1472 (w), 1300 (w), 1220 (s), 1186 (w), 1160 (w), 1114 (s), 1032 (s), 998 (s), 909 (m) cm$^{-1}$; MS (FAB$^+$) m/z 765.88 (M$^+$, 4%). Analysis calculated for C$_{28}$H$_{22}$O$_8$Cl$_8$: C, 43.67; H, 2.88. Found: C, 43.76; H, 3.01.

Compound 22e-1 was dehydrated to yield 23e in a similar way to the procedure of 22-1 to 23. The yield of 23e was 83%. $^1$H NMR (400 MHz, CDCl$_3$) for anti: δ 4.22~4.24 (m, 4H), 4.33~4.35 (m, 4H), 7.91 (s, 4H), 8.40 (s, 2H); and for syn: δ 4.24~4.28 (m, 4H), 4.35~4.39 (m, 4H), 7.84 (s, 4H), 8.19 (s, 2H). $^{13}$C NMR (100 MHz, CDCl$_3$) for anti: δ 67.41, 67.99, 77.31, 119.93, 127.66, 130.25, 131.12, 134.58, 137.63; and for syn: δ 67.42, 68.00, 77.21, 119.93, 127.62, 130.21, 131.05, 134.57, 137.56. IR (KBr) for anti: ν 3549 (w), 3472 (m), 3416 (m), 3234 (w), 2990 (w), 2905 (w), 1638 (w), 1616 (w), 1591 (w), 1282 (w), 1241 (m), 1216 (s), 1166 (w), 1121 (m) cm$^{-1}$; for syn: ν 3411 (m), 3060 (w), 2990 (w), 2904 (m), 1662 (w), 1591 (m), 1475 (w), 1336 (w), 1282 (w), 1218 (s), 1166 (m), 1121 (s), 1030 (m) cm$^{-1}$; MS (FAB$^+$) m/z 694.85 ((M+H)$^+$, 19%). Analysis calculated for compound C$_{28}$H$_{14}$O$_4$Cl$_8$: C, 48.18; H, 2.02. Found: C, 48.21; H, 2.03.

Compound 25e.

The preparation of 25e from 23e via 24e was similar to that of 25 from 23. Decomposition temperatures were 238° C. for anti and 242° C. for syn isomers. Physical data of 25e: $^1$H NMR (300 MHz, CDCl$_3$) for anti: δ 3.93~3.99 (m, 12H), 6.75 (t, J=2 Hz, 4H), 7.73 (s, 4H), 8.13 (s, 2H); for syn: δ 3.92~3.94 (m, 8H), 3.98~4.00 (m, 4H), 6.75 (t, J=2 Hz, 4H), 7.72 (s, 4H), 8.13 (s, 2H) $^{13}$C NMR (75 MHz, CDCl$_3$) for anti: δ 55.13, 64.99, 65.53, 119.71, 125.76, 130.71, 132.76, 137.92, 142.25; and for syn: δ 55.14, 65.01, 65.58, 119.73, 125.75, 130.73, 132.78, 137.97, 142.28. MS (FAB$^+$) m/z 423.16 ((M+H)$^+$, 100%). Analysis calculated for C$_{28}$H$_{22}$O$_4$: C, 78.85; H, 6.14. Found: C, 79.22; H, 5.70.

Tetracene Derivatives.

Tetracene has also been approved as a useful p-type gate material for OTFT applications. Its soluble precursors containing carbonyl bridges have been prepared in this work as well. As indicated in the general formula C, there are 12 possible substituents indicated as $R_1$~$R_8$, which denote substituents such as hydrogen, methyl, cyano, methoxy, phenyl, fluoro, chloro, bromo atoms or groups. Specific examples are given as $R_1$~$R_8$ of numbers 1~28 in Table 1.

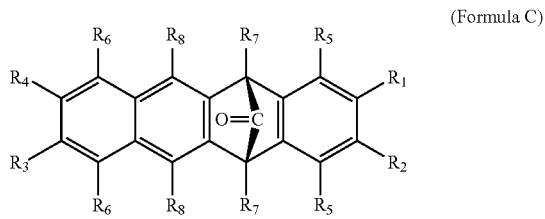

(Formula C)

A carbonyl adduct of tetrocene, i.e., compound 34, was also synthesized. This compound can extrude a molecule of CO, either upon heating or under light irradiation, to generate highly pure tetracene. The synthetic scheme is demonstrated according to the following series of reactions:

(0.99 g, 65%). $^1$H NMR (400 MHz, $CDCl_3$): δ 3.06 (s, 3H), 3.26 (s, 3H), 4.02 (t, J=2.2 Hz, 2H), 6.72 (t, J=2.2 Hz, 2H), 7.02 (dd, J=3.1, 5.1 Hz, 2H), 7.24 (dd, J=3.1, 5.1 Hz, 2H).

Compound 33:

In a round bottom flask compound 32 (100 mg, 0.49 mmole) was dissolved in dry DMF (15 mL) under a nitrogen atmosphere, then it was heated to 90-100° C. A mixture of 1,2-bis(dibromomethyl)benzene (1.04 g, 2.5 mmole) and sodium iodide (1.48 g, 9.9 mmole) was added gradually into the above solution. It was heated for a period of 48 hr, then was cooled. The resulting mixture was poured into an aqueous solution of 20% sodium thiosulfate, then was extracted several times with dichloromethane. The organic layers were combined, washed twice with distilled water, dried over anhydrous $MgSO_4$, and evaporated in vacuo. The brown solids were purified with silica gel chromatograph eluted with hexane/ethyl acetate to gave compound 33 which appeared as pale yellow solids (21 mg, 14%). $^1$H NMR (400 MHz, $CDCl_3$): δ 3.20 (s, 3H), 3.23 (s, 3H), 4.58 (s, 2H), 7.04 (m, 2H), 7.31 (m, 2H), 7.38 (m, 2H), 7.66 (s, 2H), 7.67 (s, 2H).

Compound 34.

To a round bottom flask containing acetone (10 mL) was added compound 33 (21 mg, 0.070 mmole), sodium iodide (104 mg, 0.70 mmole), and cerium chloride hydrate (258 mg,

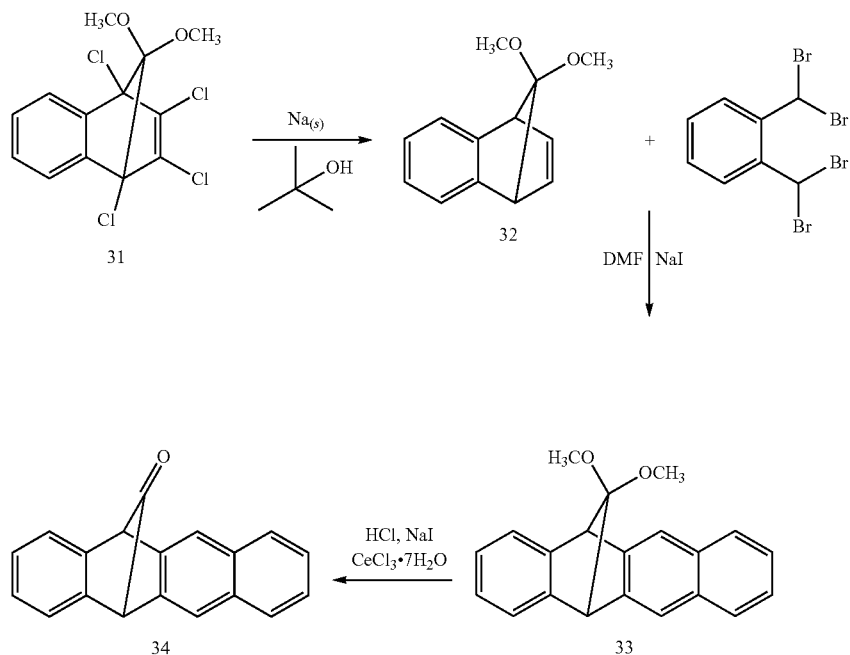

Compound 32.

To a two-necked round bottom flask fitted with a refluxing condenser containing compound 31 (2.56 g, 7.5 mmole) in dry THF (150 mL) was added fresh sodium (2.60 g, 113 mmole) under a nitrogen atmosphere. The mixture was stirred at ambient temperature for 20 min, then t-butanol (4.45 g, 60 mmole) was added. The resulting mixture was heated to reflux for 20 hr. It was cooled, and the remaining sodium was filtered off. The solution was neutralized with saturated sodium bicarbonate solution, and was extracted several times with dichloromethane. The organic portions were combined, dried over anhydrous $MgSO_4$, and evaporated in vacuo. The residue was purified by silica gel chromatograph eluted with hexane/ethyl acetate to give compound 32 as white solids 0.70 mmole), followed by a small amount of concentrated hydrochloric acid (0.2 mL). The mixture was stirred at room temperature for 3 days. The solution was neutralized by saturated sodium bicarbonate solution, and was extracted several times with dichloromethane. The organic portions were combined, washed with brine, dried over anhydrous $MgSO_4$, and evaporated in vacuo. Compound 34 was collected as pale yellow solids (16.1 mg, 91%). $^1$H NMR (400 MHz, $CDCl_3$): δ 4.88 (s, 2H), 7.18-7.20 (m, 2H), 7.44-7.46 (m, 2H), 7.48-7.50 (m, 2H), 7.79-7.81 (m, 2H), 7.89 (s, 2H).

Anthracene Derivatives.

Anthracene with a CO bridging across 4a,8a-positions, i.e., compound expressed by formula D where $R_1$=H, is known. The substituents $R_{14}$ can be modified to certain aromatic groups or aryl substituted ethenyl groups. This group of compounds can be expressed by a general formula D, in which $R_{14}$ is a kind of substituent at the diagonal positions.

TABLE 3

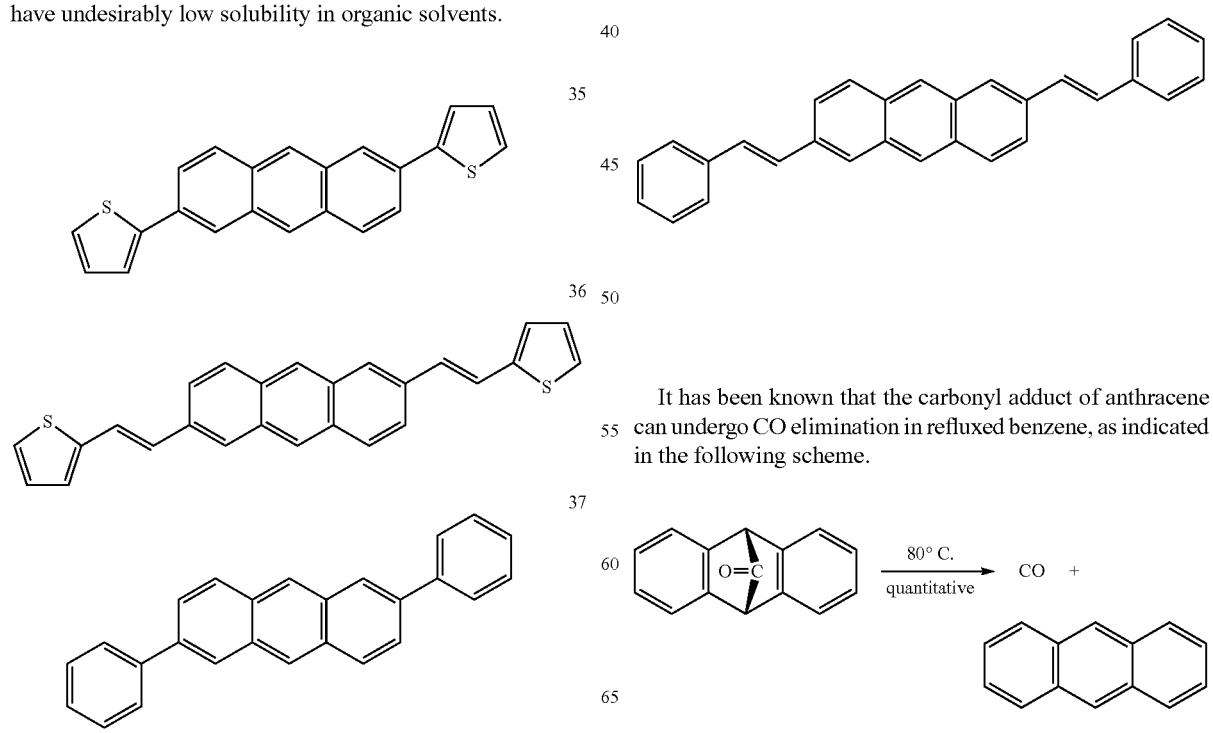

Substituents for $R_{14}$ as indicated in formula D for anthracene derivatives.

While anthracene derivatives 35, 36, 37 and 38 have been shown to exhibit good p-type OTFT characteristics, they all have undesirably low solubility in organic solvents.

It has been known that the carbonyl adduct of anthracene can undergo CO elimination in refluxed benzene, as indicated in the following scheme.

The following carbonyl adducts 39-42 can be synthesized readily, and should exhibit similar CO expulsion reaction to generate the corresponding anthracene compounds 35-38 at 130° C.

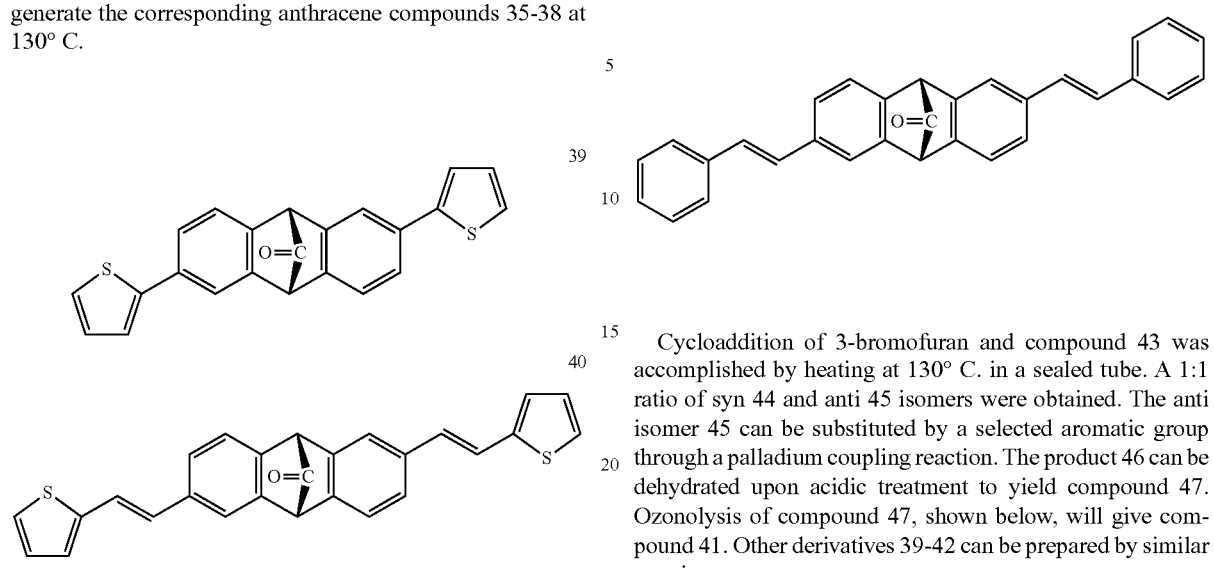

Cycloaddition of 3-bromofuran and compound 43 was accomplished by heating at 130° C. in a sealed tube. A 1:1 ratio of syn 44 and anti 45 isomers were obtained. The anti isomer 45 can be substituted by a selected aromatic group through a palladium coupling reaction. The product 46 can be dehydrated upon acidic treatment to yield compound 47. Ozonolysis of compound 47, shown below, will give compound 41. Other derivatives 39-42 can be prepared by similar reaction sequences.

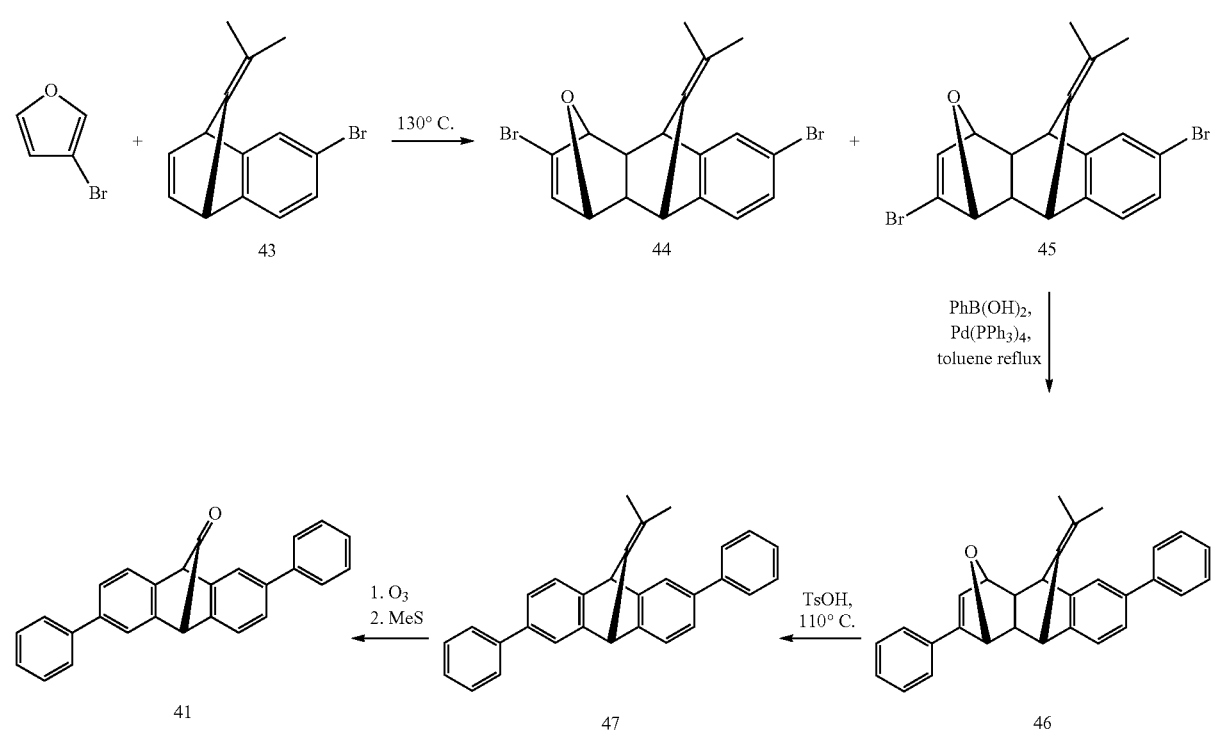

Compound 45. $^1$H NMR spectrum of compound 45 (400 MHz, CDCl$_3$) is as follows: δ 1.50 (s, 3H), 1.65 (s, 3H), 2.41 (m, 1H), 2.48 (m, 1H), 3.36 (s, 1H), 3.66 (s, 1H), 4.54 (m, 1H), 4.80 (m, 1H), 6.15 (s, 1H), 6.92 (d, J=8 Hz, 1H), 7.11 (d, J=8 Hz, 1H), 7.21 (s, 1H). $^{13}$C NMR (100 MHz, CDCl$_3$): δ 19.85, 22.84, 43.88, 44.20, 47.90, 48.69, 81.92, 84.49, 116.66, 118.74, 121.35, 123.15, 125.72, 128.18, 131.13, 144.39, 148.08, 151.26.

CO Expulsion by Both Thermal and Photochemical Methods.

All the carbonyl adducts reported herein are reactive either thermally of photochemically. Thermal fragmentation promoted by heating can be traced by TGA or DSC scans. FIGS. 3A and 3B clearly show the production of pentacene from compounds 1 and 2 upon irradiation with light.

An advantage of photo over thermal methods for CO expulsion is that the former can be used on photo-lithography. A patterned thin film of pentacene can be made by first spin-coating a thin film of the precursors, then the film is covered by a mask to prevent light from passing through. The film with mask is placed under light, while the areas without mask will be converted into insoluble pentacene. After the mask is removed, and the chemical film is washed with solvent to dissolve the un-reacted precursors, a film of pentacene with a desired pattern of the mask is obtained.

What is claimed is:

1. A tetracene derivative comprising formula C:

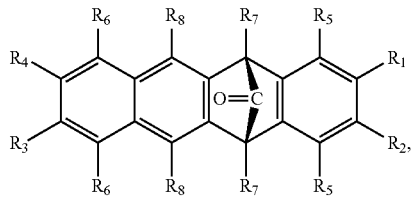

wherein $R_1$-$R_8$ are independently selected from the group consisting of hydrogen, methyl, cyano, methoxy, phenyl, fluoro, chloro, and bromo, and
wherein at least two of $R_1$-$R_8$ are not hydrogen.

2. A method of forming a film on a substrate comprising:
applying a composition to form a film on the substrate, the composition comprising a tetracene derivative according to claim 1; and
expelling volatile units of CO or $CO_2$ from the film by at least one of: thermally treating the film and photochemically treating the film.

3. The method of claim 2, wherein the applying comprises spin-coating to form a film.

4. The method of claim 2, wherein the composition further comprises at least one organic solvent.

5. The method of claim 2, further comprising masking at least a portion of the film before expelling volatile units of CO or $CO_2$ from the film by photochemically treating the film.

6. The method of claim 5, further comprising removing the mask and washing the film with a solvent after photochemically treating the film.

7. A tetracene derivative according to claim 1, wherein the tetracene derivative comprises $R_1$-$R_8$ as selected from the group consisting of numbers 1-27 according to the table:

| No. | $R_1$ | $R_2$ | $R_3$ | $R_4$ | $R_5$ | $R_6$ | $R_7$ | $R_8$ |
|---|---|---|---|---|---|---|---|---|
| 1 | $CH_3$ | $CH_3$ | H | H | H | H | H | H |
| 2 | $CH_3$ | H | $CH_3$ | H | H | H | H | H |
| 3 | $CH_3$ | $CH_3$ | $CH_3$ | $CH_3$ | H | H | H | H |
| 4 | $CH_3$ | $CH_3$ | $CH_3$ | $CH_3$ | $CH_3$ | $CH_3$ | H | H |
| 5 | Cl | Cl | H | H | H | H | H | H |
| 6 | Cl | H | Cl | H | H | H | H | H |
| 7 | Cl | Cl | H | H | Cl | H | H | H |
| 8 | Cl | Cl | Cl | Cl | H | H | H | H |
| 9 | Cl | Cl | Cl | Cl | Cl | H | H | H |
| 10 | Cl | Cl | Cl | Cl | Cl | Cl | H | H |
| 11 | F | F | H | H | H | H | H | H |
| 12 | F | H | F | H | H | H | H | H |
| 13 | F | F | H | H | F | H | H | H |
| 14 | F | F | F | F | H | H | H | H |
| 15 | F | F | F | F | F | H | H | H |
| 16 | F | F | F | F | F | F | H | H |
| 17 | F | F | F | F | F | F | F | F |
| 18 | F | F | F | F | F | F | F | F |
| 19 | CN | CN | H | H | H | H | H | H |
| 20 | CN | H | CN | H | H | H | H | H |
| 21 | CN | CN | CN | CN | H | H | H | H |
| 22 | $OCH_3$ | $OCH_3$ | H | H | H | H | H | H |
| 23 | $OCH_3$ | H | $OCH_3$ | H | H | H | H | H |
| 24 | $OCH_3$ | $OCH_3$ | $OCH_3$ | $OCH_3$ | H | H | H | H |
| 25 | $OCH_3$ | H | CN | H | H | H | H | H |
| 26 | $OCH_3$ | $OCH_3$ | CN | CN | H | H | H | H |
| 27 | Ph | H | Ph | H | H | H | H | H. |

* * * * *